US011657903B2

(12) United States Patent
McBratney et al.

(10) Patent No.: US 11,657,903 B2
(45) Date of Patent: May 23, 2023

(54) METHOD OF QUANTIFYING SOIL CARBON

(75) Inventors: Alex McBratney, New South Wales (AU); Budiman Minasny, New South Wales (AU); Jaap De Gruijter, Wageningen (NL); Philip James Mulvey, New South Wales (AU)

(73) Assignee: THE UNIVERSITY OF SYDNEY, New South Wales (AU)

( * ) Notice: Subject to any disclaimer, the term of this patent is extended or adjusted under 35 U.S.C. 154(b) by 732 days.

(21) Appl. No.: 13/701,786

(22) PCT Filed: Jun. 6, 2011

(86) PCT No.: PCT/AU2011/000702
§ 371 (c)(1),
(2), (4) Date: Mar. 27, 2013

(87) PCT Pub. No.: WO2011/150472
PCT Pub. Date: Dec. 8, 2011

(65) Prior Publication Data
US 2013/0197814 A1    Aug. 1, 2013

(30) Foreign Application Priority Data
Jun. 4, 2010   (AU) ................................ 2010902472

(51) Int. Cl.
*G16C 20/20*        (2019.01)
*G16C 99/00*        (2019.01)
(Continued)

(52) U.S. Cl.
CPC ............. *G16C 20/20* (2019.02); *G01N 33/24* (2013.01); *G06Q 10/06* (2013.01); *G16C 99/00* (2019.02)

(58) Field of Classification Search
CPC ...................................................... G06F 19/70
(Continued)

(56) References Cited

U.S. PATENT DOCUMENTS 3,508,877 A  *  4/1970 Hood ..................... G01N 31/00
                                                           436/155
RE37,066 E  *  2/2001 Casey .................... E21B 33/127
                                                           73/864.44

(Continued)

OTHER PUBLICATIONS

Miklos, M. et al, "Mapping and comparing the distribution of soil carbon under cropping and grazing management practices in Narrabri north-west New South Wales", Australian Journal of Soil Research, May 6, 2010, vol. 48, pp. 248-257.*

(Continued)

*Primary Examiner* — Lina M Cordero
(74) *Attorney, Agent, or Firm* — Neal, Gerber & Eisenberg LLP

(57) ABSTRACT

One aspect of the present disclosure relates to a method of quantifying soil carbon in a unit of land. The method generally comprises the steps of (i) obtaining an estimated spatial distribution of carbon content in the unit of land, (ii) stratifying the unit of land into a plurality of strata based at least partly on the spatial distribution of carbon content, (iii) selecting one or more locations from each of one or more of the plurality of strata, the one or more locations being selected with randomness, (iv) determining sample carbon content associated with the one or more first locations and (v) determining total carbon content in the unit of land based at least partly on the sample carbon content. In another aspect, this method may be used to quantify soil carbon sequestered in a unit of land by repeating steps (iv) and (v) at a second time and thereafter determining the amount of carbon sequestered. Furthermore, in quantifying the soil carbon sequestered, steps (ii) and (iii) may also be repeated at the second time after re-stratification of the unit of land based on sample carbon determined at the first time.

25 Claims, 20 Drawing Sheets

(51) Int. Cl.
*G01N 33/24* (2006.01)
*G06Q 10/06* (2023.01)

(58) Field of Classification Search
USPC .......................................................... 702/23
See application file for complete search history.

(56) References Cited

U.S. PATENT DOCUMENTS

| | | | |
|---|---|---|---|
| 7,457,758 B2 | 11/2008 | Zimmerman | |
| 2006/0088939 A1* | 4/2006 | Rajendram | G01N 21/31 436/31 |
| 2008/0311611 A1* | 12/2008 | Michaels | C12Q 1/04 435/29 |
| 2010/0040260 A1* | 2/2010 | Kelle | G06V 10/267 382/110 |
| 2011/0055220 A1* | 3/2011 | Tyburski | G01N 33/0004 707/743 |
| 2011/0076356 A1* | 3/2011 | Ziemer | C12R 1/01 426/2 |

OTHER PUBLICATIONS

Simbahan, G. C. et al. "Sampling optimization based on secondary information and its utilization in soil carbon mapping" Geoderma, 2006, vol. 133, pp. 345-362.*

Peltoniemi, M. et al. "Stratification of Regional Sampling by Model-Predicted Changes of Carbon Stocks in Forested Mineral Soils" Silva Fennica, 2007, vol. 41(3), pp. 527-539.*

Simbahan, G. C. et al. "Fine-resolution mapping of soil organic carbon based on multivariate secondary data" Geoderma, 2006, vol. 132, pp. 471-489.*

Graham, et. al., Fire and Terrain Controls on Soil Carbon in Chaparral Watersheds, 2001-2006 Mission Kearney Foundation of Soil Science: Soil Carbon and California's Terrestrial Ecosystems Final Report: 2002019, Jan. 1, 2003-Dec. 31, 2004; Nov. 2007.*

Gibbs et al., Monitoring and estimating tropical forest carbon stocks: making REDD a reality, 2007, Environ. Res. Lett. 2 045023.*

McKenzie—Sampling, Measurement and Analytical Protocols for Carbon Estimation in Soil, Litter and Coarse Woody Debris, 2000.*

Laura Pla, Determining Stratum Boundaries with Multivariate Real Data, Biometrics, vol. 47, No. 4 (Dec. 1991), 1409-1422 (Year: 1991).*

M. Miklos et al, "Mapping and comparing the distribution of soil carbon under cropping and grazing management practices in Narrabri north-west New South Wales", Australian Journal of Soil Research, May 6, 2010, vol. 48, pp. 248-253, 256-257, Figures.

S.B. Bird et al, "Spatial herterogeneity of aggregate stability and soil carbon in semi-arid rangeland", Environmental Pollution, 2002, vol. 116, pp. 445-455.

E.G. Jobbagy et al< "The vertical distribution of soil organic carbon and its relation to climate and vegetation", Ecologial Application, 2000, vol. 10, No. 2, pp. 423-436.

B.P. Malone et al, "Mapping continuous depth functions of soil carbon storage and available water capacity", Geoderma, 2009, vol. 154, pp. 138-152.

A.B. Mcbratney et al, "On digital soil mapping", Geoderma, 2003, vol. 117 pp. 3-52.

T. Dalenius et al, "Minimum variance stratification", Journal of the American Statistical Association, 1959, vol. 54, pp. 88-101.

European Search Report for Application No. EP 11 788 990.7 dated Nov. 3, 2016, 8 pages.

* cited by examiner

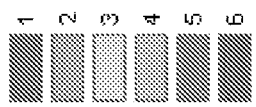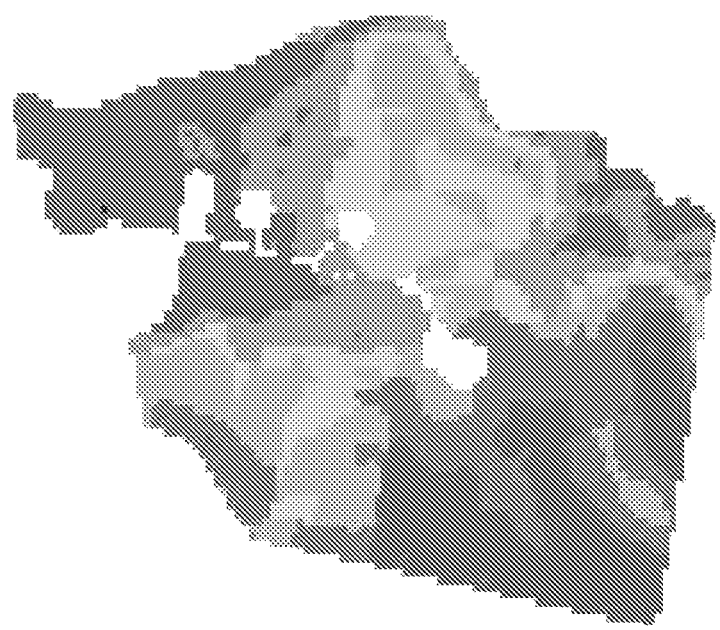
Figure 3

| Variable | Description of variable | Notes |
|---|---|---|
| $\Delta FC_{storage}$ | Change in carbon storage at the farm scale between time 1 & 2 | |
| $AD_{mass}$ | Total 'layer' weight | Air dry weight (or 40°C 48 hrs). For compositing must be additions of equal mass |
| $AD_{soil}$ | Total AD soil weight | Material <2mm size (Total weight – gravel = <2mm AD soil) |
| $C\%$ | Carbon concentration | Using HCl treatment to remove inorganic carbonates when pH is >7.5 |
| $C_{content}$ | Carbon content of stratum to standard mass per unit area | |
| $C_{dens}$ | Carbon content per layer | C% * OD soil component |
| $C_{dens\,i}$ | Cumulative carbon mass by layer | |
| $C_{dens1}$ | C density at either layer adjacent to standard mass | i.e. layer 1 nearest above standard depth, layer 2 nearest below |
| $C_{mass}$ | Carbon content per layer | C% * OD soil component |
| $C_{mass\,i}$ | Cumulative carbon mass by layer | |
| $C_{mass1}$ | C mass at either layer adjacent to standard mass | i.e. layer 1 nearest above standard mass, layer 2 nearest below |
| $C_r$ | Core shoe radius | Needed to scale up to stratum or representative area (m² here) |
| $C_{St}$ | Average carbon mass per unit area per stratum | |
| $C_{STdens}$ | Carbon content to standard volume | |
| $C_{STdens\,k}$ | Composite carbon masses to standard volume | |
| $C_{STmass}$ | Carbon content to standard mass | |
| $C_{STmass\,k}$ | Composite carbon masses to standard mass per strata | |
| $FC_{content}$ | Farm scale carbon content | |
| $G_v$ | Gravel volume | Material > 2mm size |
| $G_w$ | Gravel weight | Material > 2mm size |
| $k$ | Cores per composite | |

Figure 4A

| Variable | Description of variable | Notes |
|---|---|---|
| $L_l$ | Layer length | |
| $L_{ST}$ | Standard length (100cm) | |
| $L_v$ | Layer volume | |
| $m$ | Number of composites | |
| $mdd\Delta\%FC_{content}$ | 95% confidence interval for % difference in farm scale carbon content (here assuming equal variance between time 1&2) | |
| $mdd\Delta FC_{content}$ | Minimum detectable difference in farm scale carbon content (here assuming equal variance between time 1&2) | |
| $mdd\Delta FC_{storage}$ | Minimum detectable difference in farm scale carbon storage (here assuming equal variance between time 1&2) | |
| $n$ | Number of cores within the strata | |
| $OD_{mass}$ | OD mass weight | OD soil weight + gravel weight |
| $OD_{mass\ i}$ | Cumulative OD mass by layer | |
| $OD_{mass1}$ | OD mass at either layer adjacent to standard mass | i.e. layer 1 nearest above standard mass, layer 2 nearest below |
| $OD_{soil}$ | OD soil weight | AD soil <2mm corrected for moisture content |
| $OD_{STmass}$ | Standard mass (oven dry) | |
| $pH$ | pH | If pH is >7.5 need to correct for inorganic carbon |
| $S(C_{St})$ | Standard error of average carbon mass per unit volume by stratum | |
| $SP_{BD}$ | Soil and pore bulk density | |
| $SP_v$ | Soil and pore volume | |
| $St_a$ | Stratum area | |
| $t_1$ & $t_2$ | Sampling at time 1 and at time 2 | |

Figure 4B

| Variable | Description of variable | Notes |
| --- | --- | --- |
| v | Standard area | i.e. a single core is scaled to 1m$^2$ |
| v | Standard volume | i.e. a single core is scaled to 1m$^3$ |
| $V(\Delta FC_{storage})$ | Variance of change in carbon storage at the farm scale between time 1 & 2 | |
| $S(\Delta FC_{storage})$ | Standard error of change in carbon storage at the farm scale between time 1 & 2 | |
| $V(C_{content})$ | Variance of carbon content of stratum to standard mass per unit area | |
| $V(C_{St})$ | Variance of average carbon mass per unit volume by stratum | |
| $V(FC_{content})$ | Variance of farm scale carbon content | |
| θ | Soil moisture | Soil moisture content |
| ρ | temporal autocorrelation coefficient of errorless measurements (equal to 0 since samples are independent) | |

Figure 4C

| Core ID | Layer ID | $AD_{mass}$ | $G_w$ | $AD_{soil}$ | $\theta$ | $OD_{soil}$ | C%* | $OD_{mass}$ | $OD_{soil}$ | $C_{mass}$ | $OD_{mass\ i}$ | $C_{mass\ i}$ WO 2011/150472 |
|---|---|---|---|---|---|---|---|---|---|---|---|---|
| Eq. | | | | (1.1) | | (1.2) | | (1.3) | (1.4) | (1.5) | (1.6) | (1.7) |
| units | | g | g | g | g/g | g | % | $kg^{-1}.m^{-2}$ | $kg^{-1}.m^{-2}$ | $kg^{-1}.m^{-2}$ | $kg^{-1}.m^{-2}$ | $kg^{-1}.m^{-2}$ |
| 2i | 1 | 881.2 | 17.32 | 863.88 | 0.01 | 856.01 | 1.01 | 770.05 | 754.78 | 5.77 | 770.05 | 5.77 |
| 2i | 2 | 610.85 | 37.29 | 573.56 | 0.04 | 553.23 | 0.54 | 520.69 | 487.81 | 2.62 | 1290.74 | 8.39 |
| 2i | 3 | 527.78 | 83.3 | 444.48 | 0.03 | 431.74 | 0.59 | 454.13 | 380.68 | 2.25 | 1744.87 | 10.63 |

*C% refers to TC%, corrected for IC% if pH over ~7

| Core ID | $OD_{STmass}$ | $C_{STmass}$ | v | n | St | $C_{St}$ | $V(C_{St})$ | $S(C_{St})$ | $St_a$ | $C_{content}$ | $V(C_{content})$ |
|---|---|---|---|---|---|---|---|---|---|---|---|
| Eq. | | (1.8)* | | | | (1.9) | (1.10) | (1.11) | | (1.12) | (1.13) |
| Units | $kg^{-1}.m^{-2}$ | $kg^{-1}.m^{-2}$ | $m^{-2}$ | count | nominal | $kg^{-1}.m^{-2}$ | $C^2 kg^{-2}.m^{-4}$ | $kg^{-1}.m^{-2}$ | $m^{-2}$ | Mg/stratum | $kg^{-2}.m^{-4}$/stratum |
| 1e | 1500 | 14.20 | 1 | | 1 | 15.44 | 0.67 | 0.82 | 857850 | 13245.59 | 493441054447.78 |
| 1f | 1500 | 16.98 | 1 | | 2 | 10.29 | 0.19 | 0.44 | 752970 | 7747.12 | 107704290439.99 |
| 1g | 1500 | 15.14 | 1 | 3 | | | | | | | |
| 2k | 1500 | 10.65 | 1 | | | | | | | | |
| 2a | 1500 | 10.79 | 1 | | | | | | | | |
| 2i | 1500 | 9.42 | 1 | 3 | | | | | | | |

* here linear interpolation has been used except where recovered $OD_{mass}$ is insufficient to meet $OD_{STmass}$ in which case additional mass is assumed to contain no additional organic carbon.

Figure 5C

| Farm totals | $FC_{content}$ | $V(FC_{content})$ | $S(FC_{content})$ | +/-95% CI | $mdd\Delta\%\ FC_{content}$* | $mdd\Delta\ FC_{content}$* | $mdd\Delta\ FC_{storage}$* |
|---|---|---|---|---|---|---|---|
| Eq. | (1.14) | (1.15) | (1.16) | (1.17) | (1.18)* | (1.19) | (1.20) |
| Units | Mg | $Mg^{-2}$ | Mg | Mg | % | Mg | $kg^{-1}.m^{-2}$ |
| | 20992.71 | 601145.34 | 775.34 | 1557.65 | 10.49 | 2202.85 | 1.37 |

*assuming equal variance between time 1 & 2

Figure 5D

| Core ID | Layer ID | v | $AD_{mass}$ | $G_w$ | $AD_{soil}$ | θ | $OD_{soil}$ | C%* | $OD_{mass}$ | $OD_{soil}$ | $C_{mass}$ | $OD_{mass\ i}$ | $C_{mass\ i}$ |
|---|---|---|---|---|---|---|---|---|---|---|---|---|---|
| Eq. | | | | | (2.1) | | (2.2) | | (2.3) | (2.4) | (2.5) | (2.6) | (2.7) |
| units | | | g | g | g | g/g | g | % | $kg^{-1}.m^2$ | $kg^{-1}.m^2$ | $kg^{-1}.m^2$ | $kg^{-1}.m^2$ | $kg^{-1}.m^2$ |
| 2a+2i | 1 | 2 | 530.49 | 20.94 | 509.55 | 0.008 | 505.30 | 1.581 | 232.00 | 222.77 | 3.52 | 232.00 | 3.52 |
| 2a+2i | 2 | 2 | 1087.32 | 24.77 | 1062.55 | 0.012 | 1049.71 | 0.507 | 473.71 | 462.79 | 2.35 | 705.71 | 5.87 |
| 2a+2i | 3 | 2 | 2353.27 | 158.81 | 2194.46 | 0.036 | 2115.53 | 0.573 | 1002.69 | 932.68 | 5.34 | 1708.40 | 11.21 |

*C% refers to TC%, corrected for IC% if pH over ~7

| Core ID | $OD_{STmass}$ | $C_{STmass}$ | v | k | $vC_{STmass}$ | St | n | m | $C_{ST}$ | $V(C_{St})$ | $S(C_{St})$ | $St_a$ | $C_{content}$ | $V(C_{content})$ |
|---|---|---|---|---|---|---|---|---|---|---|---|---|---|---|
| Eq. | | (2.8) | | | (2.9) | | | | (2.10) | (2.11) | (2.12) | | (2.13) | (2.14) |
| Units | $kg^{-1}.m^{-2}$ | $kg^{-1}.m^{-2}$ | $m^2$ | count | $kg^{-1}$ | nominal | count | count | $kg^{-1}.m^{-2}$ | $C\,kg^{-2}.m^{-4}$ | $kg^{-1}.m^{-2}$ | $m^2$ | Mg/stratum | $kg^{-2}.m^{-4}$/stratum |
| 1e | 1500 | 14.24 | 1 | 1 | 14.24 | 1 | 3 | 2 | 14.212 | 0.001 | 0.023 | 857850 | 12192.05 | 3755581260.10 |
| 1f+1g | 1500 | 14.2 | 1 | 2 | 28.39 | 2 | 3 | 2 | 10.219 | 0.029 | 0.169 | 752970 | 7694.60 | 16218715439.67 |
| 2k | 1500 | 10.46 | 1 | 1 | 10.46 | | | | | | | | | |
| 2a+2i | 1500 | 10.1 | 1 | 2 | 20.20 | | | | | | | | | |

Figure 6C

| Farm totals | $FC_{content}$ | $V(FC_{content})$ | $S(FC_{content})$ | +/-95% CI | $\Delta\% FC_{content}$* | $\Delta FC_{content}$* | $mdd\Delta FC_{storage}$* |
|---|---|---|---|---|---|---|---|
| Eq. | (2.15) | (2.16) | (2.17) | (2.18) | (2.19) | (2.20) | (2.21) |
| Units | Mg | $Mg^2$ | Mg | Mg | % | Mg | $kg^{-1}.m^{-2}$ |
| | 19886.65 | 16594.30 | 128.82 | 258.80 | 1.84 | 365.99 | 0.23 |

*assuming equal variance between time 1 & 2

Figure 6D

| Core ID | Layer ID | AD$_{mass}$ | G$_w$ | AD$_{soil}$ | θ | OD$_{soil}$ | L$_l$ | L$_v$ | G$_v$ | SP$_v$ | SP$_{BD}$ | C%* | C$_{dens}$ | C$_{dens\ l}$ | C$_{dens\ i}$ |
|---|---|---|---|---|---|---|---|---|---|---|---|---|---|---|---|
| Eq. | | | | (1.1) | | (1.2) | | (1.3) | (1.4) | (1.5) | (1.6) | | (1.7) | (1.8) | (1.9) |
| units | | g | g | g | g/g | g | cm | cm$^{-3}$ | cm$^{-3}$ | cm$^{-3}$ | g$^{-1}$.cm$^{-3}$ | % | g$^{-1}$.cm$^{-3}$ | layer kg$^{-1}$.m$^{-3}$ | kg$^{-1}$.m$^{-3}$ |
| 2i | 1 | 881.2 | 17.32 | 863.88 | 0.01 | 856.01 | 54 | 612.42 | 6.54 | 605.88 | 1.41 | 1.01 | 0.0143 | 7.71 | 7.71 |
| 2i | 2 | 610.85 | 37.29 | 573.56 | 0.04 | 553.23 | 35 | 396.94 | 14.07 | 382.87 | 1.44 | 0.54 | 0.0078 | 2.73 | 10.44 |
| 2i | 3 | 527.78 | 83.3 | 444.48 | 0.03 | 431.74 | 25.5 | 289.20 | 31.43 | 257.77 | 1.67 | 0.59 | 0.0099 | 2.52 | 12.96 |

*C% refers to TC%, corrected for IC% if pH over ~7

| Core ID | $L_{ST}$ | $C_{STdens}$ | v | n | St | $C_{St}$ | $V(C_{St})$ | $S(C_{St})$ | $St_a$ | $C_{content}$ | $V(C_{content})$ |
|---|---|---|---|---|---|---|---|---|---|---|---|
| Eq. | (1.10) | | | | | (1.11) | (1.12) | (1.13) | | (1.14) | (1.15) |
| Units | cm | $kg_1^-.m_3^-$ | $m_3^-$ | count | nominal | $kg_1^-.m^{-3}$ | $C\,kg_2.m^{-6}$ | $kg_1^-.m^{-3}$ | $m^{-2}$ | Mg/stratum | $kg^{-2}.m^{-6}$/stratum |
| 1e | 100 | 14.47 | 1 | | 1 | 15.35 | 0.306 | 0.553 | 857850 | 13164 | 225416325308 |
| 1f | 100 | 16.37 | 1 | | 2 | 10.60 | 0.314 | 0.560 | 752970 | 7981 | 17803187406 |
| 1g | 100 | 15.19 | 1 | 3 | | | | | | | |
| 2k | 100 | 11.57 | 1 | | | | | | | | |
| 2a | 100 | 10.59 | 1 | | | | | | | | |
| 2i | 100 | 9.63 | 1 | 3 | | | | | | | |

Figure 7C

| Farm totals | $FC_{content}$ | $V(FC_{content})$ | $S(FC_{content})$ | +/-95% CI | Δ%FC content* | ΔFC content* | mddΔFC storage* |
|---|---|---|---|---|---|---|---|
| Eq. | (1.16) | (1.17) | (1.18) | (1.19) | (1.20) | (1.21) | (1.22) |
| Units | Mg | $Mg^{-2}$ | Mg | Mg | % | Mg | $kg^{-1}.m^{-2}$ |
| | 21066.03 | 468542.59 | 684.50 | 1375 | 9.2 | 1944.78 | 1.21 |

*assuming equal variance between time 1 & 2

Figure 7D

| Core ID | $AD_{mass}$ | $G_w$ | $AD_{soil}$ | $\theta$ | $OD_{soil}$ | $L_l$ | k | $L_v$ | $G_v$ | $SP_v$ | $SP_{BD}$ | C% | C dens | C dens i |
|---|---|---|---|---|---|---|---|---|---|---|---|---|---|---|
| Eq. | | | (2.1) | | (2.2) | | | (2.3) | (2.4) | (2.5) | (2.6) | | (2.7) | (2.8) |
| units | g | g | g | g/g | g | cm | count | $cm^{-3}$ | $cm^{-3}$ | $cm^{-3}$ | $g \cdot cm^{-3}$ | % | $g^{-1} \cdot cm^{-3}$ | layer $kg^- \cdot m^{-2}$ |
| 2a+2i | 3971.08 | 204.52 | 3766.56 | 0.076 | 3670.54 | 114.25 | 2 | 2591.45 | 77.18 | 2514.28 | 1.46 | 0.69 | 0.0101 | 11.55 |

Figure 8A

| Core ID | $L_{ST}$ | $C_{STdens}$ | v | k | St | n | m | $C_{St}$ | $V(C_{St})$ | $S(C_{St})$ | $St_a$ | $C_{content}$ | $V(C_{content})$ |
|---|---|---|---|---|---|---|---|---|---|---|---|---|---|
| Eq. | | (2.9)* | | | | | | (2.10) | (2.11) | (2.12) | | (2.13) | (2.14) |
| Units | cm | $kg^{-1} \cdot m^{-3}$ | $m^{-3}$ | count | nominal | count | count | $kg^{-1} \cdot m^{-3}$ | $C\,kg^{-2} \cdot m^{-6}$ | $kg^{-1} \cdot m^{-3}$ | $m^2$ | Mg/stratum | $kg^{-2} \cdot m^{-6}$/stratum |
| 1e | 100 | 14.20 | 1 | 1 | 1 | 3 | 2 | 15.39 | 0.713 | 0.844 | 857850 | 13202.62 | 524571556906 |
| 1f+1g | 100 | 15.99 | 1 | 2 | 2 | 3 | 2 | 10.53 | 0.354 | 0.595 | 752970 | 7931.58 | 200966584345 |
| 2k | 100 | 11.38 | 1 | 1 | | | | | | | | | |
| 2a+2i | 100 | 10.11 | 1 | 2 | | | | | | | | | |

Figure 8B

| Farm totals | FC$_{content}$ | V(FC $_{content}$) | S(FC $_{content}$) | +/-95% CI | Δ% FC $_{content*}$ | Δ FC $_{content*}$ | mdd Δ FC $_{storage*}$ |
|---|---|---|---|---|---|---|---|
| Eq. | (2.15) | (2.16) | (2.17) | (2.18) | (2.19) | (2.20) | (2.21) |
| Units | Mg | Mg$^{-2}$ | Mg | Mg | % | Mg | kg$^{-1}$.m$^{-2}$ |
|  | 21134.2 | 725538.1 | 851.8 | 1711.2 | 11.45 | 2420.05 | 1.50 |

*assuming equal variance between time 1 & 2

Figure 8C

METHOD OF QUANTIFYING SOIL CARBON

PRIORITY CLAIM

This application is a national stage application of PCT/AU2011/000702, filed on Jun. 6, 2011, which claims the benefit of and priority to Australian Patent Application No. 2010902472, filed on Jun. 4, 2010, the entire contents of which are each incorporated by reference herein.

BACKGROUND

In the context of carbon emissions offset trading schemes there is a need for a statistically and economically viable method for the auditing of soil carbon change over a designated time period for a unit of land. This facilitates transparency in the emitter sequesterer contracts and provides confidence to the market, the general public and the government.

One method suggested by the NSW Department of Environment, Climate Change and Water (DECCW) for obtaining such an estimate is the quadrat method. For a given or designated unit of land, a 25 m by 25 m subarea is chosen and divided into 10 by 10 equal sized quadrats. Ten samples are chosen at random from these 100 quadrats and the carbon concentration and soil bulk density estimated to a fixed depth of usually 50 cm. At some later date the process is repeated in the same subarea. The difference in carbon content is calculated.

The quadrat method has two drawbacks. First, the sampling area (that is, the subarea) is known, potentially leading to fraudulent practices where carbon may be deliberately sequestered in the known sampling area. More importantly, the extrapolation of the average carbon content from the smaller subarea to the larger unit of land under sequestration management leads to a large sampling variance resulting in an uncertain estimate of the change in carbon content.

SUMMARY

The present disclosure relates generally to a method of quantifying soil carbon, and particularly to a method of quantifying soil carbon based on a sampling strategy.

According to a first aspect of the present disclosure there is provided a method of quantifying soil carbon in a unit of land, the method comprising the steps of:
  obtaining an estimated spatial distribution of carbon content in the unit of land;
  stratifying the unit of land into a plurality of strata based at least partly on the spatial distribution of carbon content;
  selecting one or more locations from each of one or more of the plurality of strata, the one or more locations being selected with randomness;
  determining sample carbon content associated with the one or more locations; and
  determining total carbon content in the unit of land based at least partly on the sample carbon content.

According to a second aspect of the disclosure there is provided a method of quantifying soil carbon sequestered in a unit of land, the method comprising the steps of:
  obtaining an estimated spatial distribution of carbon content in the unit of land;
  stratifying the unit of land into a plurality of strata based at least partly on the spatial distribution of carbon content;
  selecting one or more first locations from each of one or more of the plurality of strata, the one or more first locations being selected with randomness;
  determining at a first time, first sample carbon content associated with the one or more first locations;
  determining first total carbon content in the unit of land based at least partly on the first sample carbon content;
  selecting one or more second locations from each of one or more of the plurality of strata, the one or more second locations being selected with randomness;
  determining at a second time, second sample carbon content associated with the one or more second locations;
  determining second total carbon content of the unit of land based at least partly on the second sample carbon content; and
  determining an amount of sequestered carbon in the unit of land between the first time and the second time.

According to a third aspect of the disclosure there is provided a method of quantifying soil carbon sequestered in a unit of land, the method comprising the steps of:
  obtaining an estimated spatial distribution of carbon content in the unit of land;
  stratifying the unit of land into a plurality of strata based at least partly on the spatial distribution of carbon content;
  selecting one or more first locations from each of one or more of the plurality of strata, the one or more first locations being selected with randomness;
  determining at a first time, first sample carbon content associated with the one or more first locations;
  determining first total carbon content in the unit of land based at least partly on the first sample carbon content;
  re-stratifying the unit of land into a plurality of re-stratified strata based at least partly on the first sample carbon content;
  selecting one or more second locations from each of one or more of the plurality of re-stratified strata;
  determining at a second time, second sample carbon content associated with the one or more second locations;
  determining second total carbon content in the unit of land based at least partly on the second sample carbon content; and
  determining an amount of sequestered carbon in the unit of land between the first time and the second time.

In various embodiments, the step of obtaining a spatial distribution of carbon content includes the step of obtaining a regional prediction of spatial distribution of carbon content. Alternatively or additionally the step of obtaining an estimated spatial distribution of carbon content includes the step of obtaining an estimated spatial distribution of carbon content based at least partly on information associated with the unit of land. Still alternatively or additionally the step of obtaining an estimated spatial distribution of carbon content includes the step of obtaining an estimated spatial distribution of carbon content based at least partly on any one or more of terrain information, gamma radiometric information, climate information, geologic information, regolith information, land use classification information and known soil carbon information associated with the unit of land.

In various embodiments, the method further comprises the step of downscaling the information associated with the unit of land.

In various embodiments, the step of determining sample carbon content includes the step of measuring the sample carbon content as measured sample carbon content. In one such embodiment, the step of measuring the sample carbon content includes the step of measuring the sample carbon content by combustion of soil at the one or more locations. Alternatively the step of measuring the sample carbon content includes the step of measuring the sample carbon content by near infrared spectroscopy analysis of soil at the one or more locations.

In various embodiments, the step of measuring the sample carbon content includes the step of correcting the measured sample carbon content for inorganic carbon in the soil.

In various embodiments, the step of determining sample carbon content includes the step of determining sample carbon content in one or more layers of measured mass of soil over a determined area of the unit of land. In one such embodiment, the step of determining sample carbon content includes the step of spline fitting the measured sample carbon content in three or more layers of measured mass of soil. Alternatively the step of determining sample carbon content includes determining sample carbon content based on the maximum measured sample carbon content.

In various embodiments, the step of determining sample carbon content includes the step of determining composite carbon content from two or more of said locations. Alternatively the step of determining sample carbon content includes the step of determining non-composite carbon content at each of said locations. In one such embodiment, the step of determining composite carbon content from two or more of said locations includes the step of compositing respective two or more layers of equal mass of soil from the two or more of said locations.

In various embodiments, the step of determining sample carbon content includes the step of determining sample carbon content by absolute, percentage or fractional weight or mass of carbon.

In various embodiments, the step of determining sample carbon content includes the step of determining any one or more of the average, variance and standard error of the sample carbon content across the one or more locations for each of the plurality of strata or re-stratified strata.

In various embodiments, the step of determining sample carbon content includes the step of determining any one or more of the cutting shoe diameter, push depth, pulled core length and hole depth associated with the measured mass of soil.

In various embodiments, the step of determining total carbon content includes the step of determining total carbon content in a predetermined mass of soil per unit area of the unit of land. In one such embodiment, the step of determining total carbon content includes the step of determining total carbon content in 1500 kilograms of soil per square meter of the unit of land.

In various embodiments, the step of determining total carbon content includes the step of determining total carbon content in a predetermined mass of soil per unit area of the unit of land based at least partly on the measured mass and the determined area.

In various embodiments, the step of determining total carbon content includes the step of determining any one or more of the variance, standard error, a confidence interval, a minimum detectable difference of the total carbon content in the unit of land.

In various embodiments, the step of determining an amount of sequestered carbon includes the step of determining a difference between the first total carbon content and the second total carbon content.

In various embodiments, the method further comprises the step of determining a variance, standard error or confidence interval of the sequestered carbon. In one such embodiment, the step of determining a variance, standard error or confidence interval of the sequestered carbon includes the step of determining a variance, standard error or confidence interval of the sequestered carbon based at least partly on the variance or standard error of the first sample carbon content and/or the variance or standard error of the second sample carbon content.

In various embodiments, the first time and the second time are separated by a period based at least partly on a carbon sequestration contract.

In various embodiments, the first time and the second time are separated by a period of approximately 5 years apart.

In various embodiments, the first time and the second time are separated by a period based at least partly on the minimum detectable difference of the first total carbon content in the unit of land.

In various embodiments, the step of stratifying the unit of land into a plurality of strata includes the step of stratifying the unit of land into a designated quantity or number of strata. In one such embodiment, the designated quantity or number of strata is based at least partly on any one or more of diversity of landscape, land use type, total area, and allowable uncertainty in quantifying the first total carbon content.

In various embodiments, the step of re-stratifying the unit of land into a plurality of re-stratified strata includes the step of re-stratifying the unit of land into a designated quantity or number of re-stratified strata. In one such embodiment, the designated quantity or number of re-stratified strata is based at least partly on any one or more of diversity of landscape, land use type, total area, and allowable uncertainty in quantifying the second total carbon content.

In various embodiments, the designated quantity or number of strata and/or the designated quantity or number of re-stratified strata are in the range of five to seven.

In various embodiments, the step of stratifying the unit of land into a plurality of strata includes the step of determining one or more stratum boundaries between the designated quantity or number of strata. In one such embodiment, the step of determining the one or more stratum boundaries includes the step of determining the one or more stratum boundaries based at least partly on the spatial distribution of carbon content. In one such embodiment, the step of determining the one or more stratum boundaries includes the step of determining the stratum boundaries based at least partly on a cumulative function of the square root of frequencies of occurrence of carbon derived from the spatial distribution of carbon content.

In various embodiments, the step of re-stratifying the unit of land into a plurality of re-stratified strata includes the step of determining one or more re-stratified stratum boundaries between the designated quantity or number of re-stratified strata. In one such embodiment, the step of determining the one or more re-stratified stratum boundaries includes the step of determining the one or more re-stratified stratum boundaries based at least partly on the first sample carbon content. In one such embodiment, the step of determining the one or more re-stratified stratum boundaries includes the step of determining the re-stratified stratum boundaries based at least partly on a cumulative function of the square root of the frequencies of occurrence of carbon derived from the first sample carbon content.

In various embodiments, the step of determining one or more stratum boundaries includes the step of determining one or more optimum stratum boundaries under Neyman allocation.

In various embodiments, the step of determining one or more re-stratified stratum boundaries includes the step of determining one or more optimum re-stratified stratum boundaries under Neyman allocation.

In various embodiments, the step of selecting one or more locations includes the step of determining a designated quantity or number of locations. In one such embodiment, the step of determining a designated quantity or number of locations includes the step of determining a designated number of locations based at least partly on the designated number of strata or re-stratified strata. In one such embodiment, the step of determining a designated quantity or number of locations includes the step of determining a designated quantity or number of locations to be one greater than the designated quantity or number of strata or re-stratified strata. In one such embodiment, the step of determining a designated quantity or number of locations includes the step of determining a designated quantity or number of locations to be two greater than the designated quantity or number of strata or re-stratified strata.

In various embodiments, the step of selecting one or more locations includes the step of selecting one or more locations via random sampling.

In various embodiments, the step of selecting one or more locations includes the step of selecting one or more locations from a sampling grid of locations being spaced apart by approximately 5 meters.

In various embodiments, the step of determining sample carbon content includes the step of determining sample carbon content to a sampling depth of approximately 1 meter.

In various embodiments, the unit of land includes a farm area or a catchment area.

In various embodiments, the unit of land includes a unit of land of a size between approximately 400 and approximately 3000 hectares.

In various embodiments, the carbon includes either or both of organic carbon and inorganic carbon.

In various embodiments, the carbon includes any one or more of elemental carbon, carbon oxides and carbonates.

In various embodiments, the soil includes air-dry soil and/or oven-dry soil.

Additional features and advantages are described in, and will be apparent from the following Detailed Description and the figures.

BRIEF DESCRIPTION OF THE ACCOMPANYING DRAWINGS

FIG. 3 is an example of stratification of (left) and selected locations in (right) the unit of land shown in FIG. 2E based on the estimated or predicted soil carbon distribution shown in FIG. 2G.

FIGS. 4A, 4B and 4C is a table showing a summary of variables used in calculation examples.

FIG. 5C is a table showing processed data of two strata calculated in Example 1.

FIG. 5D is a table showing processed data of the unit of land calculated in Example 1.

FIG. 6C is a table showing processed data of two strata calculated in Example 2.

FIG. 6D is a table showing processed data of the unit of land calculated in Example 2.

FIG. 7C is a table showing processed data of two strata calculated in Example 3.

FIG. 7D is a table showing processed data of the unit of land calculated in Example 3.

FIG. 8A is a table showing processed data in calculated in Example 4.

FIG. 8B is a table showing processed data of two strata calculated in Example 4.

FIG. 8C is a table showing processed data of the unit of land calculated in Example 4.

DETAILED DESCRIPTION

This present disclosure relates generally to a method of quantifying soil carbon, particularly soil organic carbon (SOC), in a unit of land. The method may be suited to a farm area or similar landscape of approximately 400 to approximately 3000 hectares. The method may be applicable to smaller and larger areas such as catchment areas. The method may be part of a soil carbon auditing protocol, in which changes in the soil carbon over a period of time may be determined by quantifying the soil carbon at the start (time $t_1$) and the end (time $t_2$) of that period. The changes in the soil carbon may be determined as the difference between the soil carbon at $t_1$ and the soil carbon at $t_2$, and may be attributed to the amount of sequestered carbon in the unit of land over that period. The soil carbon auditing protocol may be used to, for example, verify a carbon sequestration contract. This soil carbon auditing protocol is intended to enable the ascription of carbon credits to the soil body within a defined area for a defined period. Implicit within this style of auditing protocol is that it is time dependant and post event. That is, sequestered SOC may be verified for a given or designated period and traded on the basis of the agreed value to the atmosphere of that period. Such a validation system does not, in itself, offer validation of permanent or perpetual sequestration since the target variable is total carbon or total organic carbon, and not an undefined long-lived carbon fraction.

Figure 1:
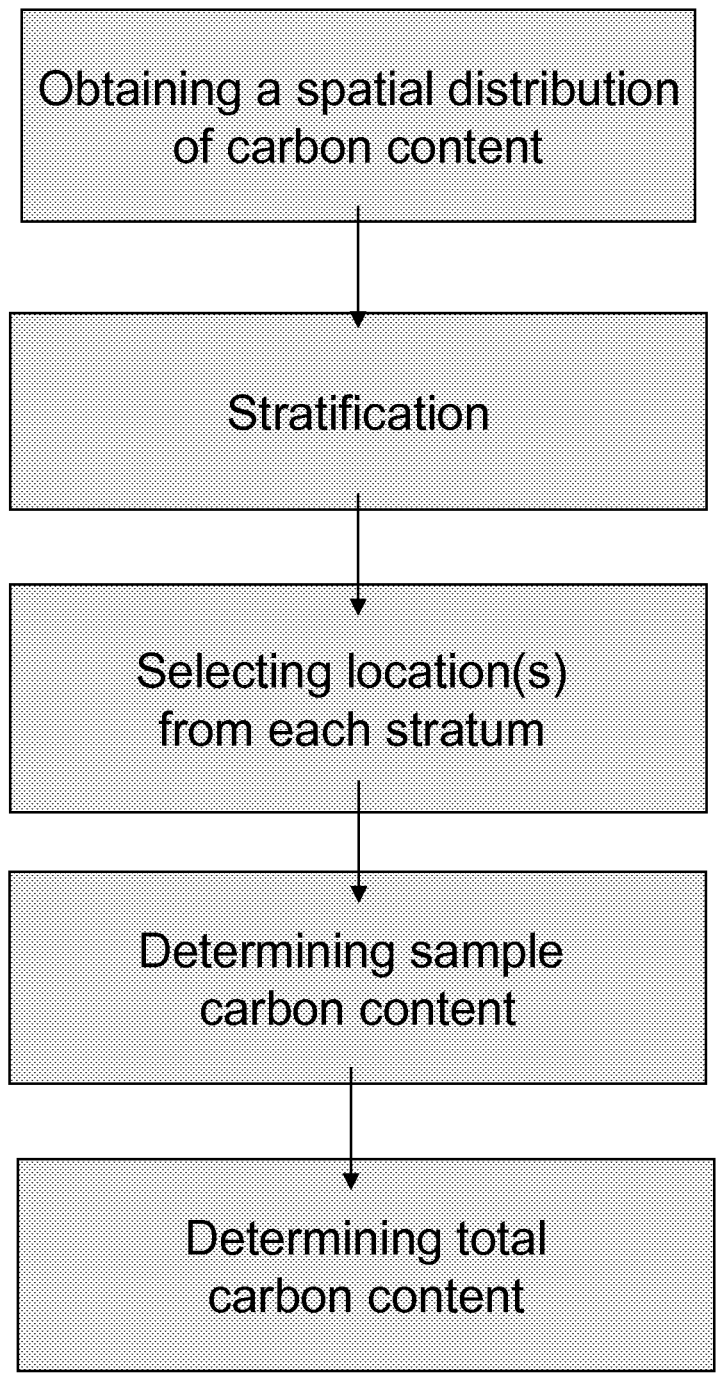
FIG. 1 is a flowchart illustrating an embodiment of the method according to the present disclosure.

Referring now to the example embodiments of the present disclosure illustrated in FIGS. 1 to 8C, as shown in FIG. 1, the method of quantifying soil carbon generally comprises the steps of (i) obtaining a spatial distribution of carbon content in the unit of land, (ii) stratifying the unit of land into a plurality of strata based at least partly on the spatial distribution of carbon content, (iii) selecting one or more first locations from each of one or more of the plurality of strata, (iv) determining at a first time first sample carbon content associated with the one or more first locations, and (v) determining first total carbon content in the unit of land based at least partly on the first sample carbon content. The first locations should be selected with randomness, for example by randomly sampling or other sampling techniques with stochasticity, to avoid fraudulent practices, such as deliberate sequestration of carbon at known or predetermined locations.

Steps (i) to (v) above relate to quantification of the soil carbon at time $t_1$ for determining, for example, the baseline carbon content. To quantify the soil carbon at time $t_2$, and hence determining the changes in the soil carbon over the period between $t_2$ and $t_1$, the method may further comprises the steps of (vi) selecting one or more second locations from each of one or more of the plurality of strata, (vii) determining at a second time second sample carbon content associated with the one or more second locations, and (viii) determining second total carbon content of the unit of land based at least partly on the second sample carbon content.

Like the first locations, the second locations may be selected with randomness. Additionally, they may be selected independent of the first locations (for example, not repeating the randomly selected first locations as the second locations) to avoid fraudulent practices.

The second time may be separated from the first time by a period determined by carbon sequestration contract, for example 5 years. The separation period may also be determined based on the minimum detectable difference associated with the first sample carbon content. For example, if the variance or standard error of the first sample carbon content is large, a longer separation period may be more sensible, since the carbon sequestered in a short period may be well under the minimum detectable difference.

The stratification for the soil carbon quantification at time $t_2$ may be based on the carbon content quantified at $t_1$, instead of the spatial distribution of carbon content obtained prior to or immediately prior to the soil carbon quantification at time $t_1$. Therefore steps (vi) to (viii) above may be replaced by the steps of (vi) re-stratifying the unit of land into a plurality of re-stratified strata based at least partly on the first sample carbon content, (vii) selecting (with randomness) one or more second locations from each of one or more of the plurality of re-stratified strata, (viii) determining at a second time second sample carbon content associated with the one or more second locations, and (vi) determining second total carbon content in the unit of land based at least partly on the second sample carbon content.

Obtaining a Spatial Distribution of Carbon Content

In order to construct the initial stratification for time $t_1$, the spatial distribution or map of soil carbon of the unit of land may be obtained by predicting or estimating the spatial distribution based at least partly on information associated with the unit of land. The prediction or estimation may be constructed using stepwise regression, or other models such as network approaches, from inputs such as:

- common terrain attributes derived from a DEM (Digital Elevation Model);
- gamma radiometrics;
- a specific landuse classification for SOC behaviour;
- various regional (250-1000 m resolution) climatic, texture and regolith layers;
- broad scale (250-1000 m resolution) regional SOC predictions; and
- prior or known SOC, or total SOC surveyed from other locations.

Generation of a soil carbon prediction for the unit of land is intended to incorporate the correlation of all available variables with soil carbon distribution into a single stratification variable—in this case the soil carbon prediction function itself. The primary reasoning behind this approach is that it avoids the troublesome drawback of traditional hierarchical 'monothetic' divisions (i.e., where each division is made in terms of a single variable beginning with the highest correlated to the lowest, which quickly leads to excessive and disjointed strata).

As a result, we use a single stratification variable: the carbon content as predicted by an appropriate model that can be applied to the class of farms for carbon auditing, resulting in 'polythetic' division. The reasoning behind this approach is that this predictor can capture the all available prior knowledge, not only about the spatial variation of the input variables, but also their relationship with carbon content as well. Typically a step-wise linear regression model is adopted to carry out this procedure. It should be appreciated that the target variable for prediction may be varied with respect to the nature and extent of the available known carbon data within a particular locale (i.e., constructed for total organic carbon density, total carbon %, total organic carbon % to a variety of spatial or mass coordinates).

Figure 2A:
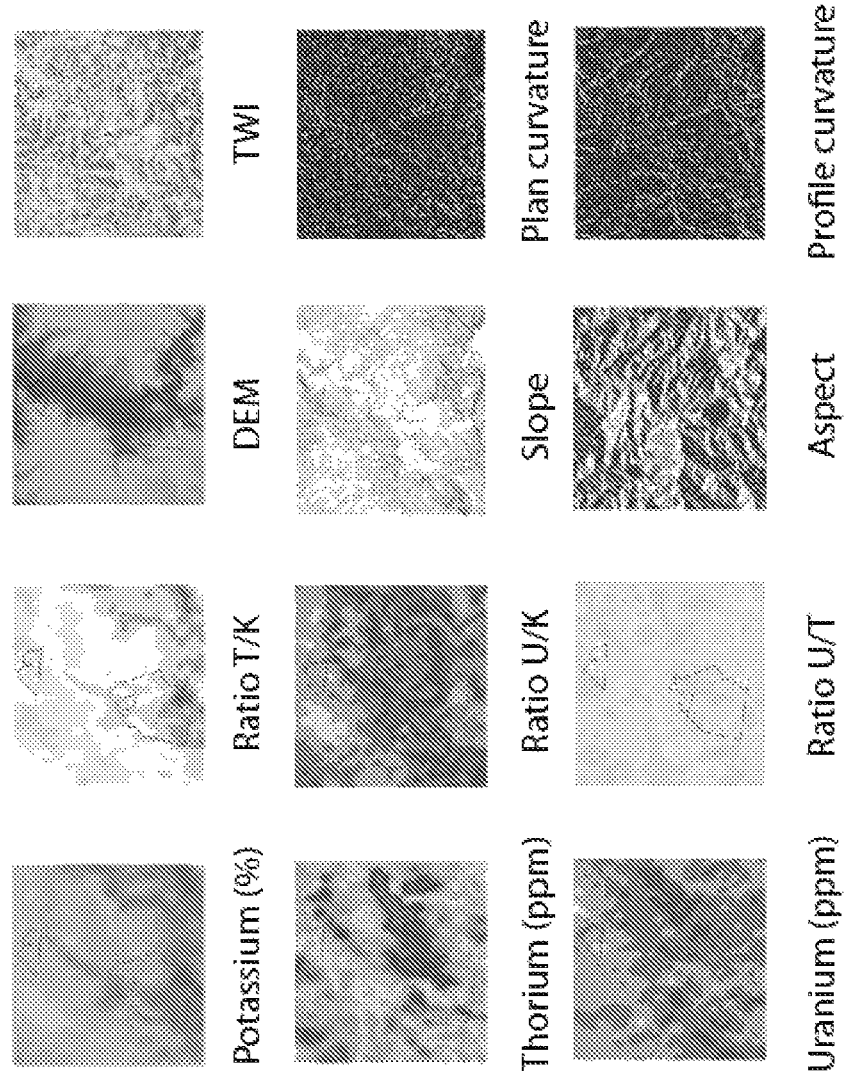
FIG. 2A are examples of landscape variables from gamma radiometrics (two leftmost columns) and attributes derived from an elevation model (two rightmost columns).
Figure 2B:
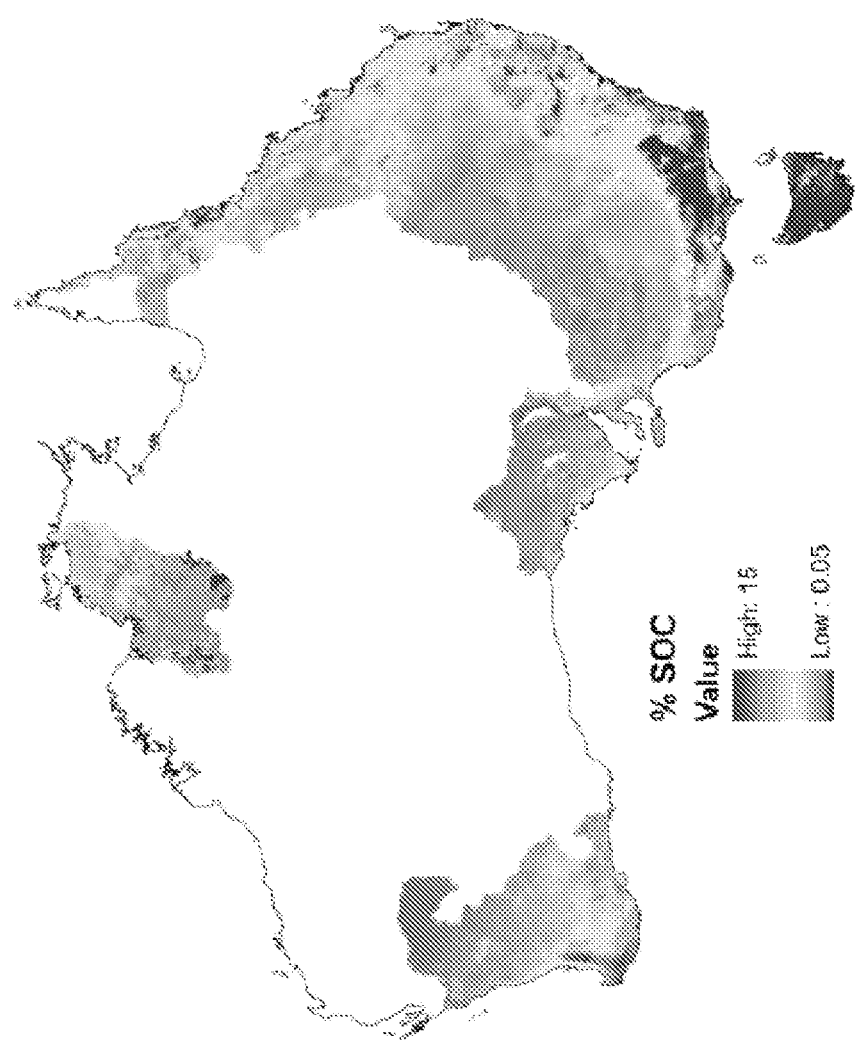
FIG. 2B is an exemplary spatial distribution of percentage topsoil organic carbon in Australia.

Typical input variables publically available for the main Australian agricultural regions include the joint METI and NASA ASTER Global Digital Elevation Model V001 and its derived terrain attributes (at 30 m resolution) and the Radiometric Map of Australia (at 100 m resolution); examples of which are depicted in FIG. 2A. In addition, other sources of information such as the topsoil and subsoil SOC % estimation (FIG. 2B) as well as climatic layers from the Australian Soil Resource Information System (ASRIS) dataset (ranging from 250 to 1000 m resolution) may also prove useful given that a wide enough spatial range of carbon observations are used to generate the carbon prediction map.

Figure 2C:
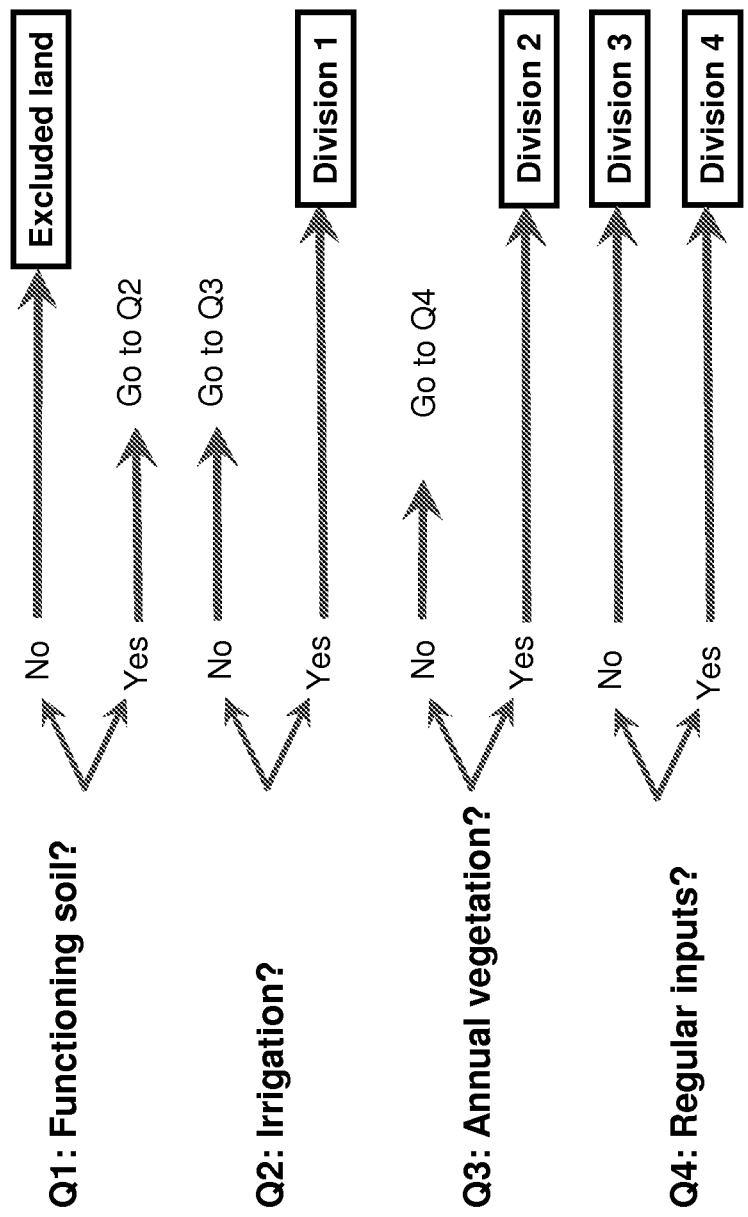
FIG. 2C are examples of primary divisions in the land use classification for soil carbon response.
Figure 2D:
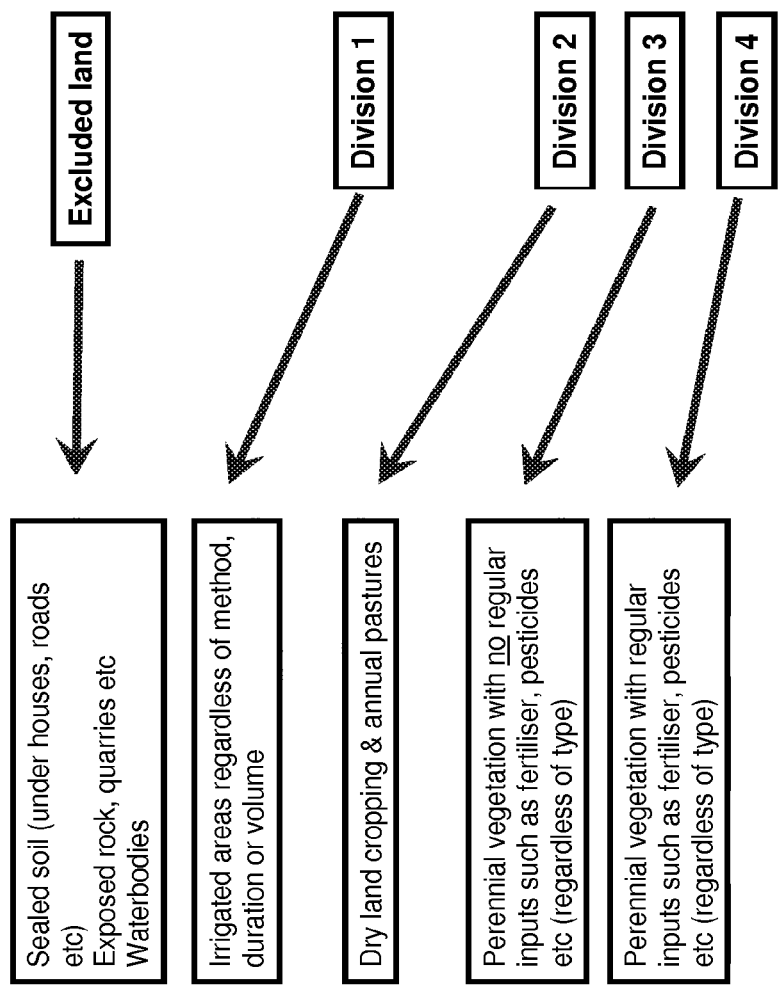
FIG. 2D are details of the primary divisions shown in FIG. 2C.
Figure 2E:
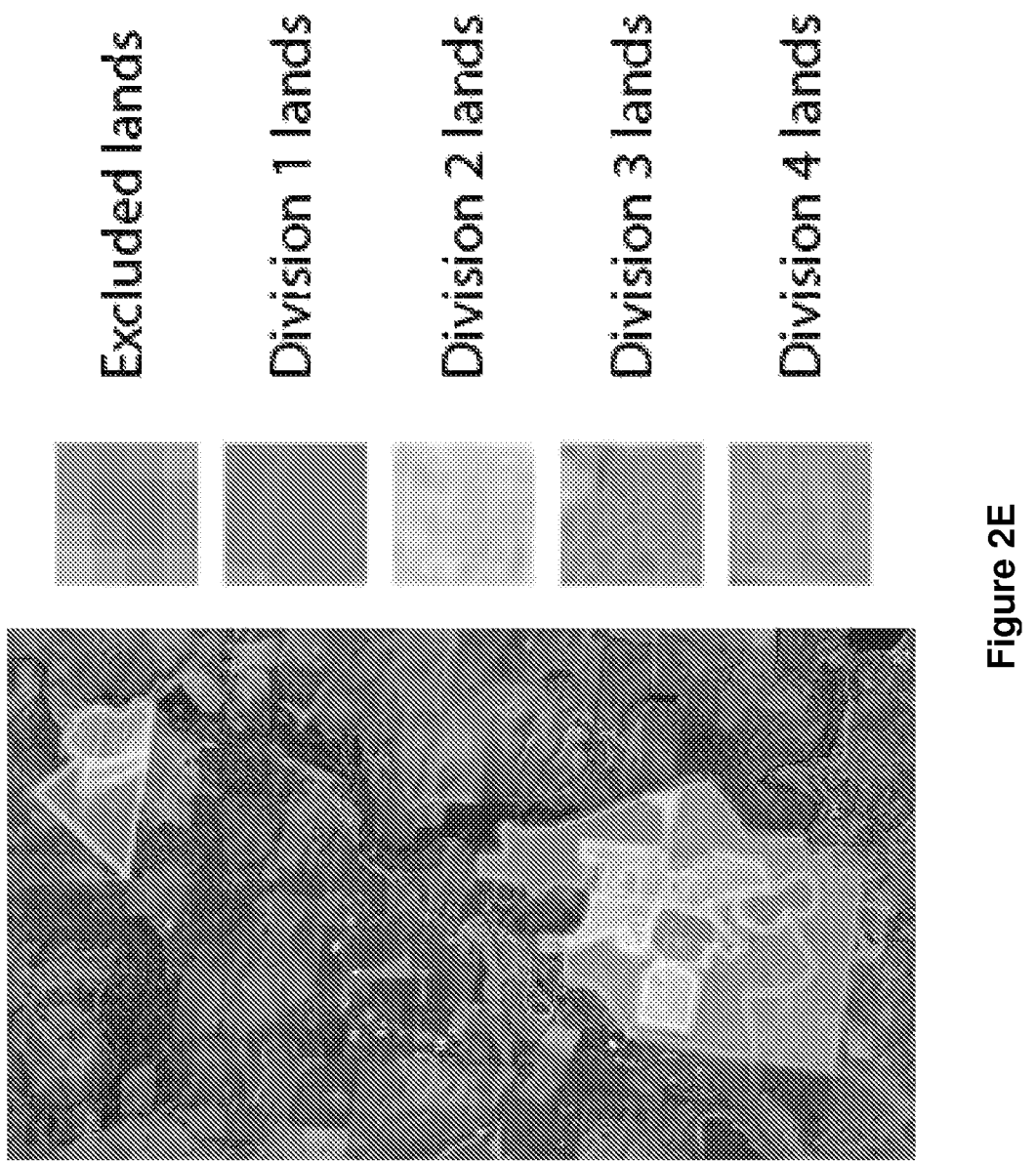
FIG. 2E is an example of a unit of land being divided into the primary divisions shown in FIG. 2C.
Figure 2F:
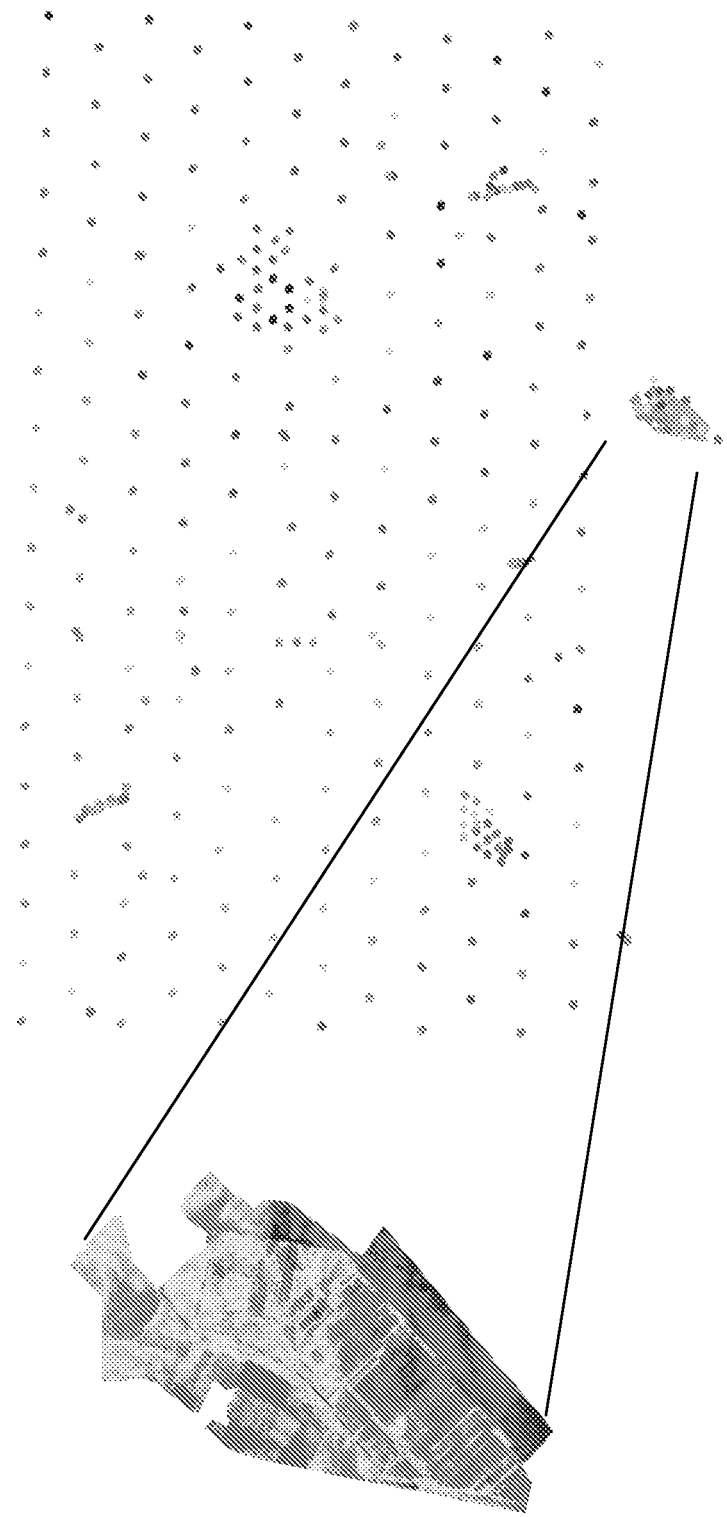
FIG. 2F is an example of prior or known soil carbon observations for constructing the prediction function for soil organic carbon.

An approach to land use classification in regards to SOC behavior has also been developed with divisions of land use classes based on a combination of known management effects on soil carbon levels and expert knowledge. The primary divisions used are: excluded lands; irrigated lands; dryland annuals; perennials with inputs and perennials with irregular inputs. A summary of the primary divisions used in this system is depicted in FIG. 2C with examples of these divisions offered in FIG. 2D. A spatial application of this classification is depicted in FIG. 2E. It should be appreciated that within the primary divisions it is possible to create sub-divisions to accommodate land uses such as tree dominated or pasture dominated perennial systems, or full tillage vs no-till dryland annual system, so that the system can evolve with increasing land use information and general system complexity. However, this process will only increase efficiency up to point, after which the divisions become too fine and its usefulness as a predictor decreases. In practice this level is determined on a case by case basis and largely relies on expert knowledge.

Figure 2G:
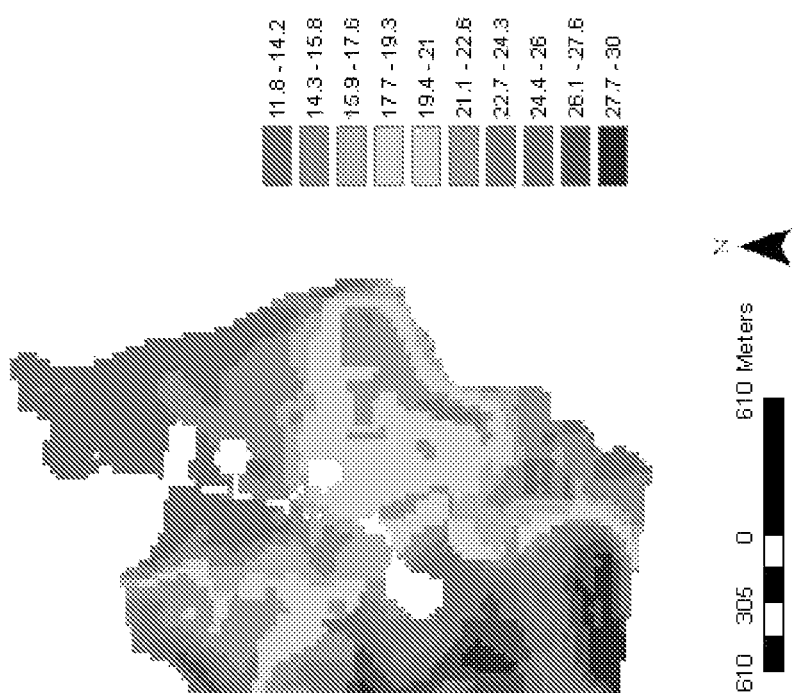
FIG. 2G is an example of estimated or predicted spatial distribution of soil organic carbon ($kg^{-1}\ m^{-3}$) in the unit of land shown in FIG. 2E.

Prior or known soil carbon information may be required to construct a soil carbon prediction map in order to map the 'best guess' at the distribution of soil carbon within the unit of land. An example of this prior information is provided in FIG. 2F. The relevant variables for each carbon observation may then be extracted from each variable layer based on spatial proximity in order to develop the soil carbon prediction function, which, in this instance was performed using step-wise regression. This particular spatial prediction function relies on relationships between an index for water accumulation in the landscape, the type of land use and the ratio of uranium to thorium within the soil/regolith. This relationship is then used to predict the soil carbon distribution across the unit of land as depicted in FIG. 2G. It should be appreciated that this prediction function need only represent the 'best available' prediction of soil carbon spatial distribution from the available data, as this process is about combining prior information into a single variable to allow polythetic division as the basis of stratification.

Furthermore the above inputs are often available at a coarse resolution. It is envisaged that the use of a downscaling process by, for example, either mechanistic or empirical functions, may transfer the inputs or data to a finer resolution and hence provide a more finely gridded or representative prediction or estimation of soil carbon. In one embodiment, the downscaling process utilizes a regional prediction of soil carbon distribution (nominally at 250 m resolution) and a computer algorithm to disaggregate regional carbon predictions using finer scale covariates (nominally at 30 m resolution) whilst preserving the soil carbon estimate made at the regional level over the target area. The computer algorithm iteratively employs weighted Generalised Additive Models (GAMs) to redistribute the soil carbon estimate onto available finer scale covariates that have some relationship with soil carbon distribution. An iterative algorithm of GAM fitting and adjustment attempts to optimize the downscaling to ensure that the target variable value given for each coarse grid cell equals the average of all target variable values at the fine scale in each coarse grid cell. In addition, it may be assumed that there is an element of uncertainty (from a range of different sources) in the data that is being downscaled. To handle this uncertainty in the downscaling process, higher weighting may be given to information which is more accurate than to information that is less accurate. The outcome of the downscaling process may provide soil carbon information on a finer scale necessary for the stratification procedure in accordance with this disclosure.

Stratification

The predicted distribution of soil organic carbon may be used for stratification of the unit of land to, for example, develop a stratified simple random sample. The purpose of this stratification is to partition the known variation of soil carbon distribution into the sampling design—an approach referred to as a design-based approach to sampling as opposed to a model-based approach to sampling. The implication of utilizing a design-based (as opposed to model-based) approach to sampling design is that actual values are considered spatially fixed and sampling points are random (model based approaches reverse these assumptions). This ensures that repeat sampling (through time) is independent and can therefore be used as a monitoring system whilst simultaneously providing verification of SOC storage through time.

The quantity or number of strata is generally determined or designated in the region of 5 to 7 given that the carbon prediction model may not be too accurate (i.e., $R^2<0.9$). The quantity or number of strata may be designated based on the diversity of the landscape, land use types, total area and the level of investment directed towards reducing the uncertainty in determining the total carbon content or carbon sequestered. Where larger properties are targeted (i.e., >2000 ha), higher quality prior data is accessible, or additional funds are available to increase the confidence in estimates it is possible to increase the quantity or number of strata used.

Once the quantity or number of strata has been determined or designated, stratum boundaries between the strata may be determined using the 'cum √f' rule. Using the predicted spatial distribution of soil carbon content for the unit of land, the stratification cut-off levels (which then determine the stratum boundaries) can be optimized for a given or designated quantity or number of strata by applying the 'cum √f' rule. This is the cumulative function of the square root of the frequencies of carbon occurrence from the predicted spatial distribution. The spatial distribution may be nominally divided into approximately 100 bins, which are then equally divided on the basis of quantity or number of strata. Internal boundaries are then converted back into original carbon units and used as the subsequent stratum break points. Stratification under the 'cum √f' rule is close to optimal for Neyman allocation. FIG. 3 (left) depicts an example of the stratification of a unit of land into six strata based on the predicted spatial distribution shown in FIG. 2G.

Re-stratification, if necessary, of the unit of land at time $t_2$ may follow similar stratification steps above. The quantity or number of re-stratified strata may be determined or designated based on the sample carbon content determined at time $t_1$. Similarly re-stratified stratum boundaries may be determined by the 'cum √f' rule applied to the sample carbon content determined at time $t_1$, instead of the predicted spatial distribution of carbon content. In one embodiment, after obtaining local scale information at the initial sampling round, the local scale information may be added to information to be stratified through various approaches including choosing the highest locally correlated covariates, updating the regional model and/or constructing local predictions, and postulating likely sequestration rates as per land use.

Selecting Locations for Determining Sample Carbon Content

A sample (with replacement) may be randomly drawn or selected at a minimum of one sampling point, and, in one such embodiment, a minimum of two sampling points (i.e., locations or composites) from within each stratum. Extra sampling points may also be drawn as backups for field decisions relating to issues such as lack of access and inappropriate locations such as dams, trees or roads that are below the practical resolution of the land use classification. Drawing sample points as close to spatially random as is practical requires creation of a finer spatial resolution of each stratum, which can be roughly equivalent to the positional accuracy of commonly available GPS equipment (i.e., 30 m resolution re-sampled to 5 m resolution before selection of random sample from each stratum).

Sample points are typically allocated equally between strata with the minimum quantity or number of sampling points informed by the need for >2 composites per stratum. Beyond this level, additional sample points are usually informed by the level of investment available and optimal levels will vary with landscape and land use. As a general rule, the quantity or number of sampling points within each stratum is determined or designated as one, and, in one such embodiment, two, greater than the total quantity or number of strata. For instance, a sample of 48 sampling points for 6 strata, with 8 sampling points per stratum, may be selected.

Once the total quantity or number of sampling units has been decided and equally allocated between strata, actual sampling points are selected using random sampling with replacement. At this point, a regular grid of spatial coordinates to a 5 m resolution is used as the basis to select points, as this is comparable to the error of common handheld GPS units whilst still yielding a reasonable sized dataset to enable greater ease of processing (i.e., a 1 m resolution grid contains 25 times the information than that of a 5 m resolution grid). The prediction function for soil carbon for instance, can only have a resolution as fine as its finest predictor (in this instance the 30 m elevation model).

FIG. 3 (right) depicts 8 randomly selected locations (with replacement) within each stratum. Soil samples are collected to maximum practical sampling depth (nominally 1 m) from within each stratum. The cutting shoe diameter (for determining the core area), push depth, pulled core length and hole depth (after extraction) are recorded for compression/expansion corrections if carbon density (as opposed to mass per area) reporting is desired.

Whole core soil samples may be physically composited within strata to reduce analysis costs. If soil samples are to be composited, the bulking process may occur within strata and yield a minimum of 2 composites, with individual air dry weight and volume recorded prior to mixing or kept separate to provide in situ information for refinement of SOC prediction and stratification for the next soil carbon quantification process. Additionally, the process of bulking, whether for a mass or a spatial coordinate system, may require that the bulked units are nominally equal in layer thickness or mass. For example, a composite may be formed by bulking a 20 cm layer of one core soil sample with a 20 cm layer of another core soil sample from the same stratum. As another example, a composite may be formed by bulking 200 g of soil from one core soil sample with 200 g of soil from another core soil sample from the same stratum. The cores may be randomly matched.

As auditing rounds progress it is expected that compositing will become the default practice due to decreasing gains in re-stratification and the economical gains of fewer analyses. However re-stratification requires careful consideration of the chosen reporting form (carbon density or mass per unit area (to standard mass) and recording of the required individual core variables). Significant changes in land use will likely require re-stratification (through processing separate samples) to reflect altered landscape patterns and adjustments of the new system before switching back to compositing.

Determining Sample and Total Carbon Content

Soil samples (whether composited, individual or sub-individual) are assessed for sample carbon content utilizing standard combustion methodologies to determine the total carbon content in the unit of land. The sample carbon content may be determined using a 53 μm Vario Max CNS analyzer, which may measure carbon content by combustion of the soil samples, or using near infrared spectroscopy analysis of the soil samples in the field. The measurement of content carbon may involve correction for inorganic carbon so that organic carbon content may be determined. The measured sample carbon content may be reported by absolute, percentage or fractional weight or mass of carbon, and may include any carbon compounds such as elemental carbon, carbon oxides and carbonates.

There are two coordinate systems for reporting total carbon content: (1) the mass or material coordinate system, and (2) the volumetric or spatial coordinate system. The mass or material coordinate system reports total carbon content in a predetermined or standard mass of soil per unit area (e.g., 1500 kg m$^{-2}$ of air dry soil) of the unit of land, whereas the volumetric or space coordinate system reports total carbon content in a predetermined or standard soil depth (e.g., 100 cm) per unit area of the unit of land.

The volumetric or spatial coordinate system is considered less advantageous due to greater variability introduced via density determination (i.e., sampling consistently to 1 m depth whilst avoiding compression or expansion and assuming consistent bulk density of soil in space is highly improbable). Therefore changes in soil carbon may be ascribed to any change in concentration, but also to a greater sampled mass with a given volume for instance.

The advantages of the mass or material coordinate system over the volumetric or spatial coordinate systems include:
- seasonal or management effects on bulk density do not confound changes in SOC storage which increases accuracy of estimates;
- a set standard reporting mass allows greater precision in determining changes in SOC storage between discrete auditing events; and
- monitoring of SOC is simpler, requiring fewer corrections and therefore reduced uncertainties.

In the instance of insufficient soil depth to obtain sufficient material mass to reach the predetermined mass or depth, any additional mass/depth added in the calculation process may be assumed to contain no additional carbon.

Examples of Total Carbon Content Calculation

For illustration purposes, examples are given below for the calculation of total carbon content using the two coordinate systems. In addition, two sub-variants of each coordinate system, constituted by a sample with and without the use of composites, are also presented.

A reduced dataset has been used for these example calculations. The reduced dataset consists of hypothetical soil sample results from 2 strata, each having 3 cores (i.e., selected locations or sampling points). Each core is divided into three layers of soil and various observations (including layer mass and depth) at each layer are made. A summary of the variables used in these examples is provided in FIG. 4. A more detailed description of the statistical theory applied in these examples is also provided in Appendix A.

EXAMPLE 1

Mass Coordinate System—Single Cores with No Composites

The mass or material coordinate approach, utilizing a standard or predetermined mass per unit area of 1500 kg·m$^{-2}$ of oven-dry mass with no compositing is presented here for the sample dataset.

Figures 5A, 5B:
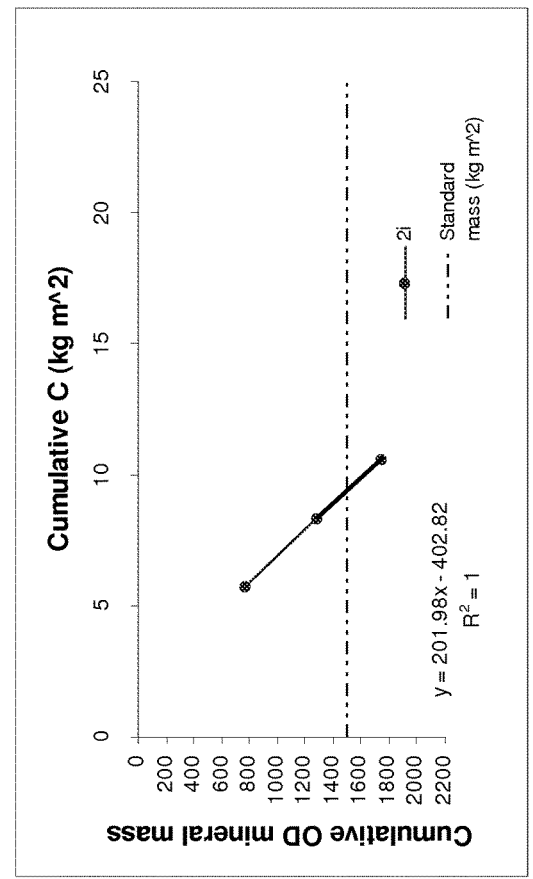
FIG. 5A is a table showing processed data of core ID "$2i$" calculated in Example 1.
FIG. 5B is a graph plotting cumulative soil mass against cumulative carbon content in Example 1.

FIG. 5A shows the sample carbon content at one of the selected locations (with core ID "$2i$") of each of the three layers as well as processed data including cumulative carbon (C) mass as a function of cumulative oven-dry (OD) soil mass for a single core as described in Eqs. 1.1-1.7.

$$AD_{mass} - G_w = AD_{soil} \quad (1.1)$$

$$AD_{soil} - (AD_{soil} \times \theta) = OD_{soil} \quad (1.2)$$

$$\left(\frac{(OD_{soil}+G_w)}{(\pi \times C_r^2)}\right) \times \frac{10000}{1000} = OD_{mass} \quad (1.3)$$

$$\left(\frac{OD_{soil}}{(\pi \times C_r^2)}\right) \times \frac{10000}{1000} = OD_{soil} \quad (1.4)$$

$$\left(\frac{OD_{soil}}{100}\right) \times C\% = C_{mass} \quad (1.5)$$

$$\sum_{l=1}^{i} OD_{mass_l} = OD_{mass_i} \quad (1.6)$$

$$\sum_{l=1}^{i} C_{mass_l} = C_{mass_i} \quad (1.7)$$

FIG. 5B depicts a linear fit interpolation to obtain C mass to the predetermined or standard mass per unit area as described in Eq. 1.8. Approaches such as spline fitting may also be used at this stage but this requires a minimum of 3 observations with mass. In this example, the sample carbon content is determined to be 9.42 kg m$^{-2}$.

$$OD_{STmass} = OD_{mass1} + (C_{STmass} - C_{mass1}) \frac{(OD_{mass2} - OD_{mass1})}{(C_{mass2} - C_{mass1})} \quad (1.8)$$

In some instances where insufficient soil mass is recovered, the preference is not to use an extrapolation method but to take the maximum C mass obtained and assume any additional mass to reach the standard contains no additional carbon.

Eqs. 1.9 to 1.13 and FIG. 5C illustrate the determination of average or mean sample carbon content, its variance and standard error (normalized to the predetermined or standard mass) across the three selected locations in each stratum (core ID's 1$e$, 1$f$ and 1$g$ in Stratum 1 and core ID's 2$k$, 2$a$ and 2$i$ in Stratum 2).

$$\left(\frac{1}{(v \times n)}\right) \times \left(\sum_{k=1}^{m} C_{STmass_k}\right) = C_{St} \quad (1.9)$$

$$\left(\frac{1}{(n-1)nv^2}\right) \times \left\{\sum_{k=1}^{m} \frac{C_{STmass_k}^2}{n_k} - \frac{1}{n}\left(\sum_{k=1}^{m} C_{STmass_k}\right)^2\right\} = V(C_{St}) \quad (1.10)$$

$$\sqrt{V(C_{St})} = S(C_{St}) \quad (1.11)$$

$$\frac{(C_{St} \times St_a)}{1000} = C_{content} \quad (1.12)$$

$$V(C_{St}) \times St_a^2 = V(C_{content}) \quad (1.13)$$

Eqs. 1.15 to 1.20 and FIG. 5D illustrate the determination of combining sample carbon content from all strata to determine the total carbon content (including the average, variance, standard error, confidence intervals, such as a 95% confidence interval, and minimum detectable difference) in the unit of land.

$$\sum_{i=1}^{St} C_{content_i} = FC_{content} \quad (1.14)$$

$$\frac{\sum_{i=1}^{St} V(C_{content})_i}{1000000} = V(FC_{content}) \quad (1.15)$$

$$\sqrt{V(FC_{content})} = S(FC_{content}) \quad (1.16)$$

$$FC_{content} \pm t_{0.95}\sqrt{V(FC_{content})} = \pm 95\% \ C.I. \quad (1.17)$$

$$\sqrt{2} \times \left(\frac{\pm 95\% \ C.I}{\left(\frac{FC_{content}}{100}\right)}\right) = mdd\Delta \% \ FC_{content} \quad (1.18)$$

$$\left(\frac{FC_{content}}{100}\right) \times \Delta \% \ FC_{content} = mdd\Delta FC_{content} \quad (1.19)$$

$$\frac{\left(\frac{mdd\Delta FC_{content}}{1000}\right)}{\left(\sum_{i=1}^{k} St_{a_i}\right)} = mdd\Delta FC_{storage} \quad (1.20)$$

Eqs. 1.21 to 1.24 define the change in total carbon content (including the average, variance, standard error, confidence intervals, such as a 95% confidence interval) between time $t_1$ and time $t_2$.

$$FC_{content_{t1}} - FC_{content_{t2}} = \Delta FC_{storage} \quad (1.21)$$

$$\sqrt{V(FC_{content_{t1}}) + V(FC_{content_{t2}}) - 2\rho\sqrt{V(FC_{content_{t1}})}\sqrt{V(FC_{content_{t2}})}} = V(\Delta FC_{storage}) \quad (1.22)$$

$$\sqrt{V(\Delta FC_{storage})} = S(\Delta FC_{storage}) \quad (1.23)$$

$$FC_{content} \pm t_{0.95}\sqrt{V(FC_{content})} = \pm 95\% \ C.I. \quad (1.24)$$

EXAMPLE 2

Mass Coordinate System—with Composites

The mass or material coordinate approach, utilizing a predetermined or standard mass of 1500 kg·m$^{-2}$ of oven-dry mass with compositing is presented here for the sample dataset. Composites within this method require bulking of equal amounts of OD soil mass per layer. Proper randomization of composited layers (or cores) is required for this approach as estimates of average total carbon content and its variance (in particular) can be manipulated either deliberately or through unintended preference (i.e., combining similar textured or colored cores). This can be seen by comparing summary results in FIG. 5D and FIG. 6C.

Figures 6A, 6B:
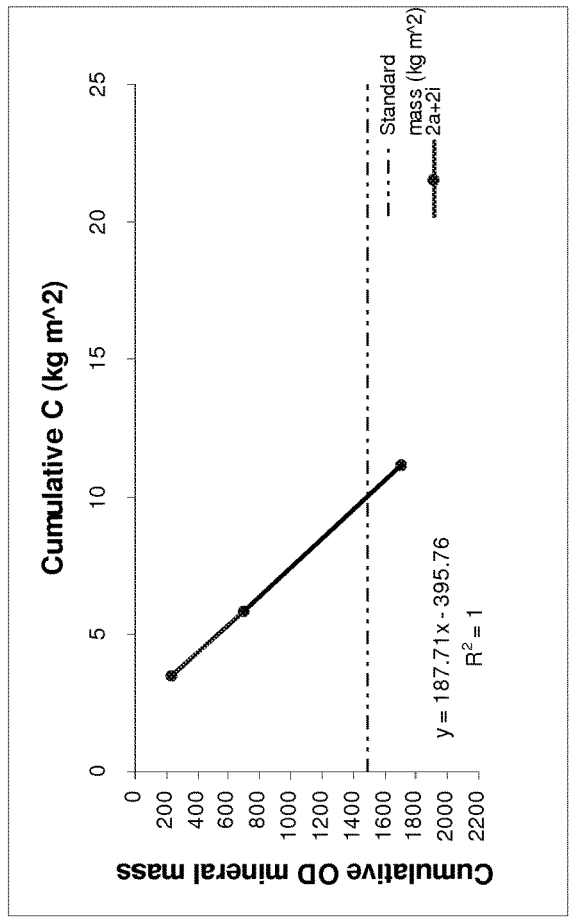
FIG. 6A is a table showing processed data of composited cores ID "$2a$" and "$2i$" calculated in Example 2.
FIG. 6B is a graph plotting cumulative soil mass against cumulative carbon content in Example 2.

FIG. 6A shows the sample carbon content of a composite of two cores (with core ID's "2$a$" and "2$i$") of each of the three layers as well as processed data including cumulative carbon (C) mass as a function of cumulative oven-dry (OD) soil mass for a composite of two cores and is described in Eqs. 2.1-2.7

$$AD_{mass} - G_w = AD_{soil} \quad (2.1)$$

$$AD_{soil} - (AD_{soil} \times \theta) = OD_{soil} \quad (2.2)$$

$$\left(\frac{(OD_{soil} + G_w)}{(\pi \times C_r^2) \times v}\right) \times \frac{10000}{1000} = OD_{mass} \quad (2.3)$$

$$\left(\frac{OD_{soil}}{(\pi \times C_r^2)}\right) \times \frac{10000}{1000} = OD_{soil} \quad (2.4)$$

$$\left(\frac{OD_{soil}}{100}\right) \times C\ \% = C_{mass} \qquad (2.5)$$

$$\sum_{l=1}^{i} OD_{mass_l} = OD_{mass_i} \qquad (2.6)$$

$$\sum_{l=1}^{i} C_{mass_l} = C_{mass_i} \qquad (2.7)$$

FIG. 6B and Eq. 2.8 illustrate a linear fit interpolation to obtain C mass to the standard mass. Approaches such as spline fitting may also be used at this stage but this requires a minimum of 3 observations with mass. In certain instances where insufficient soil mass is recovered, the preference is not to use an extrapolation method but to take the maximum C mass obtained and assume any additional mass to reach the standard contains no additional carbon. In this example, the sample carbon content of the composite is determined to be 10.22 kg m$^{-2}$.

$$OD_{STmass} = OD_{mass1} + (C_{STmass} - C_{mass1})\frac{(OD_{mass2} - OD_{mass1})}{(C_{mass2} - C_{mass1})} \qquad (2.8)$$

Eqs. 2.9 to 2.13 and FIG. 6C illustrate the determination of average carbon content, variance and standard error (to the predetermined or standard mass) across the three selected locations in each stratum (core ID's 1$e$, 1$f$ and 1$g$ in Stratum 1 and core ID's 2$k$, 2$a$ and 2$i$ in Stratum 2).

$$C_{STmass} \times k = C_{STmass_k} \qquad (2.9)$$

$$\left(\frac{1}{(nv)}\right) \times \left(\sum_{k=1}^{m} C_{STmass_k}\right) = C_{St} \qquad (2.10)$$

$$\left(\frac{1}{(m-1)nv^2}\right) \times \left\{\sum_{k=1}^{m} \frac{C_{STmass_k}^2}{n_k} - \frac{1}{n}\left(\sum_{k=1}^{m} C_{STmass_k}\right)^2\right\} = V(C_{St}) \qquad (2.11)$$

$$\sqrt{V(C_{St})} = S(C_{St}) \qquad (2.12)$$

$$\frac{(C_{St} \times St_a)}{1000} = C_{content} \qquad (2.13)$$

$$V(C_{St}) \times St_a^2 = V(C_{content}) \qquad (2.14)$$

Eqs. 2.15 to 2.21 and FIG. 6D illustrate the process of combining sample carbon content to obtain total carbon content (including variance, standard error, a confidence interval such as a 95% confidence interval) in the unit of land.

$$\sum_{i=1}^{St} C_{content_i} = FC_{content} \qquad (2.15)$$

$$\frac{\sum_{i=1}^{St} V(C_{content})_i}{1000000} = V(FC_{content}) \qquad (2.16)$$

$$\sqrt{V(FC_{content})} = S(FC_{content}) \qquad (2.17)$$

$$FC_{content} \pm t_{0.95}\sqrt{V(FC_{content})} = \pm 95\%\ C.I. \qquad (2.18)$$

$$\sqrt{2} \times \left(\frac{\pm 95\%\ C.I.}{\left(\frac{FC_{content}}{100}\right)}\right) = \Delta\ \%\ FC_{content} \qquad (2.19)$$

$$\left(\frac{FC_{content}}{100}\right) \times \Delta\ \%\ FC_{content} = \Delta FC_{content} \qquad (2.20)$$

$$\frac{\left(\frac{mdd\Delta FC_{content}}{1000}\right)}{\left(\sum_{i=1}^{k} St_{a_i}\right)} = mdd\Delta FC_{storage} \qquad (2.21)$$

Eqs. 2.22 to 2.25 define the change in total carbon content (including the average, variance, standard error, confidence intervals, such as a 95% confidence interval) between time $t_1$ and time $t_2$.

$$FC_{content_{t1}} - FC_{content_{t2}} = \Delta FC_{storage} \qquad (2.22)$$

$$V(FC_{content_{t1}}) + V(FC_{content_{t2}}) - 2\rho\sqrt{V(FC_{content_{t1}})}\sqrt{V(FC_{content_{t2}})} = V(\Delta FC_{storage}) \qquad (2.23)$$

$$\sqrt{V(\Delta FC_{storage})} = S(\Delta FC_{storage}) \qquad (2.24)$$

$$FC_{content} \pm t_{0.95}\sqrt{V(FC_{content})} = \pm 95\%\ C.I. \qquad (2.25)$$

EXAMPLE 3

Spatial Coordinate Approach—Single Cores No Composites

The volumetric or spatial coordinate approach, utilizing a standard or predetermined soil depth of 100 cm without compositing is presented here for the sample dataset.

Figures 7A, 7B:
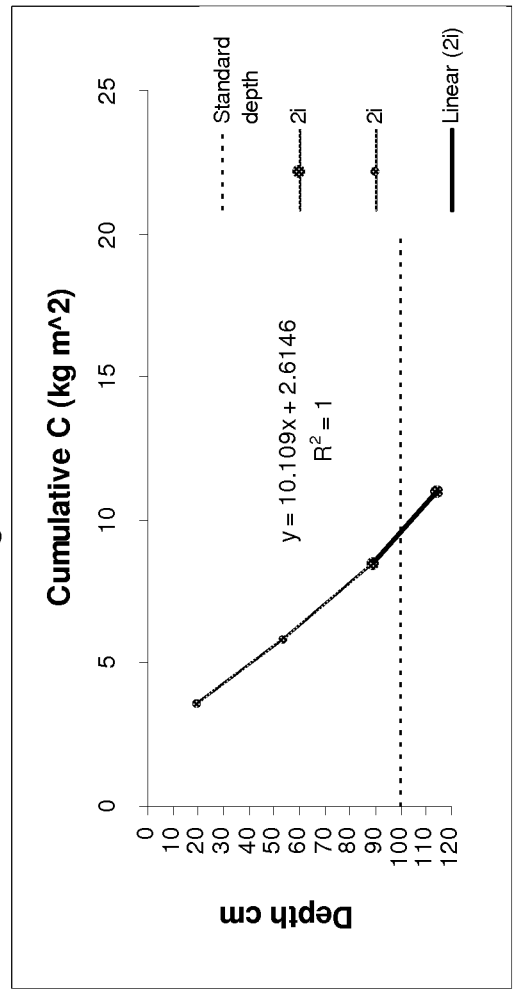
FIG. 7A is a table showing processed data of core ID "$2i$" calculated in Example 3.
FIG. 7B is a graph plotting cumulative soil depth against cumulative carbon content in Example 3.

FIG. 7A shows the sample carbon content at one of the selected locations (with core ID "2$i$") of each of the three layers as well as processed data including cumulative carbon (C) density as a function of depth for a single core is described in Eqs. 3.1-3.9.

$$AD_{mass} - G_w = AD_{soil} \qquad (3.1)$$

$$AD_{soil} - (AD_{soil} \times \theta) = OD_{soil} \qquad (3.2)$$

$$(\pi \times C_r^2) \times L_l = L_v \qquad (3.3)$$

$$\frac{G_w}{2.65} = G_v \qquad (3.4)$$

$$L_v - G_v = SP_v \qquad (3.5)$$

$$\frac{OD_{soil}}{SP_v} = SP_{BD} \qquad (3.6)$$

$$\left(\frac{C\ \%}{100}\right) \times SP_{BD} = C_{dens} \qquad (3.7)$$

$$\left(\frac{(C_{dens} \times 10000)}{1000}\right) \times L_l = C_{dens_l} \qquad (3.8)$$

$$\sum_{i=1}^{l} C_{dens_l} = C_{dens_i} \qquad (3.9)$$

FIG. 7B depicts a linear fit approach to interpolation to obtain C density to the predetermined or standard depth as described in Eq. 3.10. Approaches such as spline fitting may also be used at this stage but this requires a minimum of 3 observations with depth. In certain instances where insufficient depth is recovered, the preference is not to use an extrapolation method but to take the maximum C density obtained and assume any additional depth to reach the standard depth contains no additional carbon.

$$L_{ST} = L_{l1} + (C_{STdens} - C_{dens1})\frac{(L_{l2} - L_{l1})}{(C_{dens2} - C_{dens1})} \quad (3.10)$$

Eq. 3.11 to 3.15 and FIG. 7C illustrate the determination of average carbon content, variance and standard error (to the standard depth) across the three selected locations in each stratum (core ID's 1e, 1f and 1g in Stratum 1 and core ID's 2k, 2a and 2i in Stratum 2).

$$\left(\frac{1}{v \times n}\right) \times \left(\sum_{k=1}^{m} C_{STdens_k}\right) = C_{St} \quad (3.11)$$

$$\left(\frac{1}{(n-1)nv^2}\right) \times \left\{\sum_{k=1}^{m} \frac{C_{STdens_k}^2}{n_k} - \frac{1}{n}\left(\sum_{k=1}^{m} C_{STdens_k}\right)^2\right\} = V(C_{St}) \quad (3.12)$$

$$\sqrt{V(C_{St})} = S(C_{St}) \quad (3.13)$$

$$\frac{(C_{St} \times St_a)}{1000} = C_{content} \quad (3.14)$$

$$V(C_{St}) \times St_a^2 = V(C_{content}) \quad (3.15)$$

Eq. 3.16 to 3.22 and FIG. 7D illustrate the combining of the sample carbon content from all strata to determine the total carbon content (including the average, variance, standard error, confidence intervals, such as a 95% confidence interval, and minimum detectable difference) in the unit of land.

$$\sum_{i=1}^{St} C_{content_i} = FC_{content} \quad (3.16)$$

$$\frac{\sum_{i=1}^{St} V(C_{content})_i}{1000000} = V(FC_{content}) \quad (3.17)$$

$$\sqrt{V(FC_{content})} = S(FC_{content}) \quad (3.18)$$

$$FC_{content} \pm t_{0.95}\sqrt{V(FC_{content})} = \pm 95\% \; C.I. \quad (3.19)$$

$$\sqrt{2} \times \left(\frac{\pm 95\% \; C.I}{\left(\frac{FC_{content}}{100}\right)}\right) = \Delta \% \; FC_{content} \quad (3.20)$$

$$\left(\frac{FC_{content}}{100}\right) \times \Delta \% \; FC_{content} = \Delta FC_{content} \quad (3.21)$$

$$\frac{\left(\frac{mdd\Delta FC_{content}}{1000}\right)}{\left(\sum_{i=1}^{St} St_{a_i}\right)} = mdd\Delta FC_{storage} \quad (3.22)$$

Eqs. 3.23 to 3.26 define the change in total carbon content (including the average, variance, standard error, confidence intervals, such as a 95% confidence interval between time $t_1$ and time $t_2$.

$$FC_{content_{t1}} - FC_{content_{t2}} = \Delta FC_{storage} \quad (3.23)$$

$$\frac{V(FC_{content_{t1}}) + V(FC_{content_{t2}}) - 2\rho\sqrt{V(FC_{content_{t1}})}}{\sqrt{V(FC_{content_{t2}})}} = V(\Delta FC_{storage}) \quad (3.24)$$

$$\sqrt{V(\Delta FC_{storage})} = S(\Delta FC_{storage}) \quad (3.25)$$

$$FC_{content} \pm t_{0.95}\sqrt{V(FC_{content})} = \pm 95\% \; C.I. \quad (3.26)$$

EXAMPLE 4

Spatial Coordinate Approach—with Composites

The volumetric or spatial coordinate approach, utilizing a predetermined or standard depth of 100 cm with compositing is presented here for the sample dataset.

FIG. 8A shows the sample carbon content of a composite of two cores (with core ID's "2a" and "2i") as well as processed data including cumulative carbon (C) density as a function of depth for a composite of two cores and is described in Eqs. 4.1 to 4.8.

$$AD_{mass} - G_w = AD_{soil} \quad (4.1)$$

$$AD_{soil} - (AD_{soil} \times \theta) = OD_{soil} \quad (4.2)$$

$$(\pi \times C_r^2) \times k \times L_l = L_v \quad (4.3)$$

$$\frac{G_w}{2.65} = G_v \quad (4.4)$$

$$L_v - G_v = SP_v \quad (4.5)$$

$$\frac{OD_{soil}}{SP_v} = SP_{BD} \quad (4.6)$$

$$\left(\frac{C\%}{100}\right) \times SP_{BD} = C_{dens} \quad (4.7)$$

$$\left(\frac{(C_{dens} \times 10000)}{1000}\right) \times L_l = C_{dens_l} \quad (4.8)$$

Eq. 4.9 describes a linear fit o interpolation to obtain C density to the standard depth:

$$\left(\frac{C_{dens_l}}{L_l}\right) \times 100 = C_{STdens} \quad (4.9)$$

Eqs. 4.10 to 4.14 and FIG. 8B illustrate the determination of the average carbon content, variance and standard error (to the predetermined or standard depth) across the three selected locations in each stratum (core ID's 1e, 1f and 1g in Stratum 1 and core ID's 2k, 2a and 2i in Stratum 2).

$$\left(\frac{1}{v \times n}\right) \times \left(\sum_{k=1}^{m} C_{STdens_k}\right) = C_{St} \quad (4.10)$$

$$\left(\frac{1}{(n-1)nv^2}\right) \times \left\{\sum_{k=1}^{m} \frac{C_{STdens_k}^2}{n_k} - \frac{1}{2}\left(\sum_{k=1}^{m} C_{STdens_k}\right)^2\right\} = V(C_{St}) \quad (4.11)$$

$$\sqrt{V(C_{St})} = S(C_{St}) \quad (4.12)$$

$$\frac{(C_{St} \times St_a)}{1000} = C_{content} \quad (4.13)$$

$$V(C_{St}) \times St_a^2 = V(C_{content}) \quad (4.14)$$

Eqs. 4.15 to 4.21 and FIG. 8C illustrate the process of combining sample carbon content to obtain total carbon content (including variance, standard error, a confidence interval such as a 95% confidence interval as well as minimum detectable difference) in the unit of land.

$$\sum_{i=1}^{St} C_{content_i} = FC_{content} \quad (4.15)$$

$$\frac{\sum_{i=1}^{St} V(C_{content})_i}{1000000} = V(FC_{content}) \quad (4.16)$$

$$\sqrt{V(FC_{content})} = S(FC_{content}) \quad (4.17)$$

$$FC_{content} \pm t_{0.95}\sqrt{V(FC_{content})} = \pm 95\% \ C.I. \quad (4.18)$$

$$\sqrt{2} \times \left(\frac{\pm 95\% \ C.I}{\left(\frac{FC_{content}}{100}\right)}\right) = \Delta \% \ FC_{content} \quad (4.19)$$

$$\left(\frac{FC_{content}}{100}\right) \times \Delta \% \ FC_{content} = \Delta FC_{content} \quad (4.20)$$

$$\frac{\left(\frac{mdd\Delta FC_{content}}{1000}\right)}{\left(\sum_{i=1}^{k} St_{a_i}\right)} = mdd\Delta FC_{storage} \quad (4.21)$$

Eq. 4.22 to 4.25 define the change in total carbon content (including the average, variance, standard error, confidence intervals, such as a 95% confidence interval, and minimum detectable difference) between time $t_1$ and time $t_2$.

$$FC_{content_{t1}} - FC_{content_{t2}} = \Delta FC_{storage} \quad (4.22)$$

$$\sqrt{V(FC_{content_{t1}}) + V(FC_{content_{t2}}) - 2\rho\sqrt{V(FC_{content_{t1}})}\sqrt{V(FC_{content_{t2}})}} = V(\Delta FC_{storage}) \quad (4.23)$$

$$\sqrt{V(\Delta FC_{storage})} = S(\Delta FC_{storage}) \quad (4.24)$$

$$FC_{content} \pm t_{0.95}\sqrt{V(FC_{content})} = \pm 95\% \ C.I. \quad (4.25)$$

Having described several embodiments of the method according to the present disclosure, it should be apparent that the disclosure has the following advantages:

"System gaming" such as manipulation of soil carbon quantification results by, for example, deliberate carbon sequestration at known sampling locations is avoided by selecting sampling points with randomness.

A confidence interval (or other statistical measures such as variance) of the soil carbon may be determined so that the uncertainty in the soil carbon quantification results may be specified.

When reporting soil carbon using the mass coordinate system (i.e., using a predetermined or standard mass of soil per unit area), the compactness of the soil does not affect the soil carbon quantification results.

The method does not impede nor prescribe nor penalise changes in land use; does not impede 'real' reductions in fossil carbon emissions (due to temporary crediting for SOC).

The method reduces risk to the landholder for maintaining sequestration over indefinite periods.

The method provides an ongoing (and validated) revenue stream for landholders increasing the likelihood of SOC perpetuation.

Verification of a carbon sequestration contract for sequestered carbon can be verified for the period of time over which auditing takes place.

It will be appreciated by persons skilled in the art that numerous variations and/or modifications may be made to the disclosure as shown in the specific embodiments without departing from the spirit or scope of the disclosure as broadly described. For example, the total carbon content may be reported or normalized to a soil mass or depth other than 1500 kg m$^{-2}$ or 100 cm. The present embodiments are, therefore, to be considered in all respects as illustrative and not restrictive.

Appendix A: Theory

The estimation of SOC storage and uncertainties is inferred utilizing Weighted Least Squares regression as follows. Assume that n cores were taken from the stratum, which were used to make m composites (m>1). Let $n_k$ be the quantity or number of cores in composite k, making a volume of $x_k$ m$^3$, with a measured carbon content of $c_k$ kg. The volume of a composite equals its quantity or number of cores times the standard core volume (v): $x_k = n_k \cdot v$.

The mean carbon density of stratum j is estimated by Weighted Least Squares regression, with equation: $c = X \cdot \beta + e$, where $c = [c_1 \ldots c_k \ldots c_m]'$: the vector of carbon contents,
$X = [x_1 \ldots x_k \ldots x_n]'$: the m×1 design-matrix with composite volumes, $\beta$: the mean carbon density of the stratum, e: the vector of random errors.

WLS estimate of $\beta$: $\hat{\beta} = (X'V^{-1}X)^{-1}X'V^{-1}c$ where $V^{-1}$ is the diagonal matrix of weights, with $1/n_1, \ldots, 1/n_m$ on the diagonal, because the sampling variance of the carbon content of a composite is proportional to the quantity or number of cores.

The formula can be simplified using $$X'V^{-1} = [1 \ldots 1]v$$

$$X'V^{-1}X = nv^2$$

$$X'V^{-1}c = v\sum_{k=1}^{m} c_k$$

which leads to:

$$\hat{\beta} = \frac{1}{nv}\sum_{k=1}^{m} c_k,$$

(i.e., the total carbon content divided by the total volume of the composites).

The variance of $\beta$ is more complicated. This can be estimated by:

$$\hat{V}(\hat{\beta}) = \frac{1}{m-1} \cdot c'V^{-1}\{I - X(X'V^{-1}X)^{-1}X'V^{-1}\}c(X'V^{-1}X)^{-1}$$

which simplifies to:

$$\hat{V}(\hat{\beta}) = \frac{1}{(m-1)nv^2} \cdot \left\{\sum_{k=1}^{m} \frac{c_k^2}{n_k} - \frac{1}{n}\left(\sum_{k=1}^{m} c_k\right)^2\right\}$$

The variance estimates thus obtained for each of the strata can be imputed in $$\hat{V}(SOC_{farm}) = \sum_{h=1}^{H} a_h^2 \hat{V}(\hat{\beta}_h)$$

Where $SOC_{farm}$ is the total SOC storage on the farm, H is the quantity or number of strata, $a_h^2$ is the relative area squared of each stratum.

The standard error of the estimated mean:

$$\hat{S}(SOC_{farm}) = \sqrt{\hat{V}(SOC_{farm})}$$

Confidence intervals for SOC storage:

$$SOC_{farm} \pm t_{1-\frac{\alpha}{2}} \cdot \sqrt{\hat{V}(SOC_{farm})}$$

Simple Numerical Example for 2 Composites and 1 Stratum Utilizing a Volumetric Approach
Given sample data:
n=3
v=0.01 m³
m=2
V=[1, 2]'
X=[0.01, 0.02]' m³
c=[0.2, 0.5]'kg
Estimates:

$$\hat{\beta} = \frac{1}{3 \times 0.01}(0.2 + 0.5) = 23.33 \text{ kg} \cdot \text{m}^{-3}$$

$$\hat{V}(\hat{\beta}) = \frac{1}{2 \times 3 \times 0.01^2}\left\{\frac{0.2^2}{1} + \frac{0.5^2}{2} - \frac{1}{3}(0.2 + 0.5)^2\right\} = 2.77 \text{ kg}^2 \cdot \text{m}^{-6}$$

$$\hat{S}(\hat{\beta}) = \sqrt{\hat{V}(\hat{\beta})} = 1.66 \text{ kg} \cdot \text{m}^{-3}$$

SOC Storage Through Time

After the initial baseline audit, follow up audits are conducted at specified intervals (at roughly the same position in the annual cycle) and serve to monitor changes in SOC storage. Each successive audit may utilize the previous stratification or a newly constructed stratification, may vary the quantity or number of strata and sample units from each as long as each sample draw is random within each stratum and the minimum requirements of the methodology are met. Drawing samples from different points between time 1 and time 2 allows sampling to be independent and also reduces the likelihood of system gaming—a significant weakness of static sampling points.

A time-weighted measure of SOC storage:

$$SOC_{sequestered} = \frac{SOC_{farm}^{t2} - SOC_{farm}^{t1}}{t_2 - t_1}$$

Variance between time 1 & time 2 given independent sampling:

$$V(SOC_{farm}^{t2}) + V(SOC_{farm}^{t1}) = V(SOC_{sequestered})$$

Additionally, given that sampling is independent it can be assumed that the variance of time 1 should be equal to that of time 2, allowing the estimation of the minimum detectable difference in SOC from time 1 which can be used to inform a suitable interval period between monitoring events (i.e., if the estimate at time 1 has a large variance then the minimum detectable difference in SOC will also be larger—implying that a longer period between monitoring events would be more cost-effective).

The invention claimed is:

1. A method of quantifying soil carbon in a unit of land, the method comprising:
   (a) obtaining an estimated spatial distribution of soil carbon content in the unit of land by:
      (i) correlating information associated with the unit of land with soil carbon distribution, and
      (ii) inputting the correlated information into a soil carbon content prediction model to predict the estimated spatial distribution of soil carbon content; and
   (b) thereafter, independently auditing the obtained estimated spatial distribution of soil carbon content in the unit of land by:
      (i) stratifying, at least partially based on at least one of: a diversity of the unit of land, a land use type, and a total area of the unit of land, the unit of land into a total quantity of at least two strata, wherein the stratification includes determining one or more stratum boundaries between the total quantity of at least two strata, the determination of the one or more stratum boundaries includes determining one or more optimum stratum boundaries under Neyman allocation, and the total quantity of at least two strata is based, at least partly, on the obtained estimated spatial distribution of soil carbon content;
      (ii) after stratifying the unit of land into the total quantity of at least two strata:
         (1) determining a quantity of locations to sample within each strata, the quantity of locations to sample within each strata being at least one more than the total quantity of at least two strata and being based, at least partly, on the obtained estimated spatial distribution of soil carbon content, and
         (2) reducing sampling variance and fraudulent manipulation of soil carbon quantification results by randomly selecting, from each strata of the total quantity of at least two strata, the quantity of locations from that strata;
      (iii) using at least one of a CNS analyser and a near infrared spectroscopic analyser to determine sample soil carbon content associated with the selected quantity of locations; and
      (iv) determining total soil carbon content in the unit of land based, at least partly, on the sample soil carbon content.

2. The method of claim 1, wherein obtaining the estimated spatial distribution of soil carbon content includes obtaining a regional prediction of spatial distribution of soil carbon content.

3. The method of claim 1, which includes downscaling the information associated with the unit of land.

4. The method of claim 1, wherein determining the sample soil carbon content includes measuring the sample soil carbon content as measured sample soil carbon content.

5. The method of claim 1, wherein determining the sample soil carbon content includes determining the sample soil carbon content in one or more layers of measured mass of soil over a determined area of the unit of land.

6. The method of claim 5, wherein determining the sample soil carbon content includes determining any one or more of:

a cutting shoe diameter, a push depth, a pulled core length and a hole depth, associated with the measured mass of soil.

7. The method of claim 1, wherein determining the sample soil carbon content includes determining composite soil carbon content from two or more of the selected quantity of locations.

8. The method of claim 7, wherein determining the composite soil carbon content from two or more of the selected quantity of locations includes respectively compositing two or more layers of equal mass of soil from the two or more of the selected quantity of locations.

9. The method of claim 1, wherein determining the sample soil carbon content includes determining the sample soil carbon content by at least one of: absolute, percentage or fractional weight or mass of carbon.

10. The method of claim 1, wherein determining the total soil carbon content includes determining the total soil carbon content in a predetermined mass of soil per unit area of the unit of land.

11. The method of claim 1, wherein the total quantity of at least two strata is in a range of five to seven.

12. The method of claim 1, wherein determining the one or more stratum boundaries includes determining the one or more stratum boundaries based, at least partly, on the estimated spatial distribution of soil carbon content.

13. The method of claim 12, wherein determining the one or more stratum boundaries includes determining the one or more stratum boundaries based, at least partly, on a cumulative function of a square root of frequencies of occurrence of soil carbon derived from the estimated spatial distribution of soil carbon content.

14. The method of claim 1, wherein the information associated with the unit of land with the soil carbon distribution is selected from a group consisting of: terrain information, gamma radiometric information, climate information, geologic information, regolith information, information associated with a regional prediction of spatial distribution of soil carbon content, land use classification information and known soil carbon information associated with the unit of land.

15. The method of claim 1, wherein the determination of the total soil carbon content is further based on a confidence interval.

16. The method of claim 1, wherein the unit of land comprises at least 400 hectares associated with one carbon sequestration management contract.

17. A method of quantifying soil carbon sequestered in a unit of land, the method comprising:
(a) obtaining an estimated spatial distribution of soil carbon content in the unit of land by:
  (i) correlating information associated with the unit of land with soil carbon distribution, and
  (ii) inputting the correlated information into a soil carbon content prediction model to predict the estimated spatial distribution of soil carbon content; and
(b) thereafter, independently auditing the obtained estimated spatial distribution of soil carbon content in the unit of land by:
  (i) stratifying, at least partially based on at least one of: a diversity of the unit of land, a land use type, and a total area of the unit of land, the unit of land into a total quantity of at least two strata, wherein the stratification includes determining one or more stratum boundaries between the total quantity of at least two strata, the determination of the one or more stratum boundaries includes determining one or more optimum stratum boundaries under Neyman allocation, and the total quantity of at least two strata is based, at least partly, on the obtained estimated spatial distribution of soil carbon content;
  (ii) after stratifying the unit of land into the total quantity of at least two strata:
    (1) determining a quantity of first locations to sample within each strata, the quantity of first locations to sample within each strata being at least one more than the total quantity of at least two strata and being based, at least partly, on the obtained estimated spatial distribution of soil carbon content, and
    (2) reducing sampling variance and fraudulent manipulation of soil carbon quantification results by randomly selecting, from each strata of the total quantity of at least two strata, the quantity of first locations from that strata;
  (iii) using at least one of a CNS analyser and a near infrared spectroscopic analyser, at a first time, to determine a first sample soil carbon content associated with the selected quantity of first locations;
  (iv) determining first total soil carbon content in the unit of land based, at least partly, on the first sample soil carbon content;
  (v) after stratifying the unit of land into the total quantity of at least two strata:
    (1) determining a quantity of second locations to sample within each strata, the quantity of second locations to sample within each strata being at least one more than the total quantity of at least two strata and being based, at least partly, on the obtained estimated spatial distribution of soil carbon content, and
    (2) reducing the sampling variance and the fraudulent manipulation of the soil carbon quantification results by randomly selecting, from each strata of the total quantity of at least two strata, the quantity of second locations from that strata;
  (vi) using the at least one of the CNS analyser and the near infrared spectroscopic analyser, at a second time, to determine a second sample soil carbon content associated with the selected quantity of second locations;
  (vii) determining second total soil carbon content of the unit of land based, at least partly, on the second sample soil carbon content; and
  (viii) determining an amount of sequestered soil carbon in the unit of land between the first time and the second time.

18. The method of claim 17, wherein determining the amount of sequestered soil carbon includes determining a difference between the first total soil carbon content and the second total soil carbon content.

19. The method of claim 17, wherein the information associated with the unit of land with the soil carbon distribution is selected from a group consisting of: terrain information, gamma radiometric information, climate information, geologic information, regolith information, information associated with a regional prediction of spatial distribution of soil carbon content, land use classification information and known soil carbon information associated with the unit of land.

20. The method of claim 17, wherein at least one of the determination of the first total soil carbon content and the determination of the second total soil carbon content is further based on a confidence interval.

21. The method of claim 17, wherein the unit of land comprises at least 400 hectares associated with one carbon sequestration management contract.

22. A method of quantifying soil carbon sequestered in a unit of land, the method comprising:
  (a) obtaining an estimated spatial distribution of soil carbon content in the unit of land by:
    (i) correlating information associated with the unit of land with soil carbon distribution, and
    (ii) inputting the correlated information into a soil carbon content prediction model to predict the estimated spatial distribution of soil carbon content; and
  (b) thereafter, independently auditing the obtained estimated spatial distribution of soil carbon content in the unit of land by:
    (i) stratifying, at least partially based on at least one of: a diversity of the unit of land, a land use type, and a total area of the unit of land, the unit of land into a total quantity of at least two strata, wherein the stratification includes determining one or more stratum boundaries between the total quantity of at least two strata, the determination of the one or more stratum boundaries includes determining one or more optimum stratum boundaries under Neyman allocation, and the total quantity of at least two strata is based, at least partly, on the obtained estimated spatial distribution of soil carbon content;
    (ii) after stratifying the unit of land into the total quantity of at least two strata:
      (1) determining a quantity of first locations to sample within each strata, the quantity of first locations to sample within each strata being at least one more than the total quantity of at least two strata and being based, at least partly, on the obtained estimated spatial distribution of soil carbon content, and
      (2) reducing sampling variance and fraudulent manipulation of soil carbon quantification results by randomly selecting, from each strata of the total quantity of at least two strata, the quantity of first locations from that strata;
    (iii) using at least one of a CNS analyser and a near infrared spectroscopic analyser, at a first time, to determine a first sample soil carbon content associated with the selected quantity of first locations;
    (iv) determining first total soil carbon content in the unit of land based, at least partly, on the first sample soil carbon content;
    (v) re-stratifying the unit of land into a total quantity of at least two re-stratified strata based, at least partly, on the first sample soil carbon content;
    (vi) after re-stratifying the unit of land into the total quantity of at least two re-stratified strata, selecting a quantity of second locations from each strata of the total quantity of at least two re-stratified strata, the selected quantity of second locations being based, at least partly, on the obtained estimated spatial distribution of soil carbon content;
    (vii) using at least one of the CNS analyser and the near infrared spectroscopic analyser, at a second time, to determine a second sample soil carbon content associated with the selected quantity of second locations;
    (viii) determining second total soil carbon content in the unit of land based, at least partly, on the second sample soil carbon content; and
    (ix) determining an amount of sequestered soil carbon in the unit of land between the first time and the second time.

23. The method of claim 22, wherein the information associated with the unit of land with the soil carbon distribution is selected from a group consisting of: terrain information, gamma radiometric information, climate information, geologic information, regolith information, information associated with a regional prediction of spatial distribution of soil carbon content, land use classification information and known soil carbon information associated with the unit of land.

24. The method of claim 22, wherein at least one of the determination of the first total soil carbon content and the determination of the second total soil carbon content is further based on a confidence interval.

25. The method of claim 22, wherein the unit of land comprises at least 400 hectares associated with one carbon sequestration management contract.

* * * * *